US008523757B2

(12) United States Patent
Taub et al.

(10) Patent No.: US 8,523,757 B2
(45) Date of Patent: Sep. 3, 2013

(54) ARTERIAL DEVICE, SYSTEM AND METHOD FOR REMOVING EMBOLIC DEBRIS

(75) Inventors: Eldad Taub, Reut (IL); Nathan Sela, Modiin (IL); Benjamin Dilmoney, Givat Shmuel (IL)

(73) Assignee: Cardiogard Medical Ltd., Or-Yehuda (IL)

( * ) Notice: Subject to any disclaimer, the term of this patent is extended or adjusted under 35 U.S.C. 154(b) by 0 days.

(21) Appl. No.: 13/375,913

(22) PCT Filed: Jun. 2, 2010

(86) PCT No.: PCT/IL2010/000436
§ 371 (c)(1),
(2), (4) Date: Dec. 2, 2011

(87) PCT Pub. No.: WO2010/140150
PCT Pub. Date: Dec. 9, 2010

(65) Prior Publication Data
US 2012/0088955 A1    Apr. 12, 2012

Related U.S. Application Data

(60) Provisional application No. 61/184,019, filed on Jun. 4, 2009.

(51) Int. Cl.
*A61N 1/362* (2006.01)
*A61M 1/16* (2006.01)

(52) U.S. Cl.
USPC .............................. 600/16; 604/4.01; 604/41

(58) Field of Classification Search
USPC ..................... 606/16; 604/4.01, 43
See application file for complete search history.

(56) References Cited

U.S. PATENT DOCUMENTS

| 4,134,402 | A | | 1/1979 | Mahurkar |
| 5,425,724 | A | | 6/1995 | Akins |
| 5,584,803 | A | * | 12/1996 | Stevens et al. ............... 604/6.16 |
| 5,697,905 | A | | 12/1997 | d'Ambrosio |

(Continued)

FOREIGN PATENT DOCUMENTS

WO    2005123158 A1    12/2005

OTHER PUBLICATIONS

International Search Report published Sep. 12, 2010 for PCT/IL2010/000436.
Written Opinion published Apr. 12, 2011 for PCT/IL2010/000436.

(Continued)

*Primary Examiner* — Christopher D Koharski
*Assistant Examiner* — Michael Carey
(74) *Attorney, Agent, or Firm* — Workman Nydegger

(57) ABSTRACT

An arterial device, system and method are provided for use with a patient undergoing a cardiac procedure. The system is configured for enabling one or more arterial devices to be accommodated in the aorta of the patient in use of the system, and a perfusion lumen arrangement provides therethrough a target perfusion flow into the aorta having a target perfusion flow rate that is significantly greater than a nominal perfusion flow rate, by an excess perfusion flow rate. A suction lumen arrangement provides therethrough a suction flow out of the aorta at a suction flow rate. The target perfusion flow rate and the suction flow rate may be concurrently and selectively controlled to cause embolic debris that may be present in the aorta to be diverted to the suction inlet, while providing the nominal flow rate to the body circulation of the patient.

23 Claims, 15 Drawing Sheets

(56) References Cited

U.S. PATENT DOCUMENTS

| | | |
|---|---|---|
| 6,689,149 B2 | 2/2004 | Maahs |
| 6,726,651 B1 | 4/2004 | Robinson et al. |
| 7,470,363 B2 | 12/2008 | Milo |
| 2002/0111583 A1 | 8/2002 | Wright |
| 2002/0138031 A1* | 9/2002 | Ross .......................... 604/4.01 |
| 2003/0221561 A1* | 12/2003 | Milo ............................ 96/175 |

OTHER PUBLICATIONS

International Preliminary Report published Jun. 12, 2011 for PCT/IL2010/000436.

Mia N. Andersen et al, Quantitative haemodynamic evaluation of aortic cannulas, Perfusion 2004; vol. 19, pp. 323-330.

* cited by examiner

SECTION 0-0

SECTION 2-2

SECTION 4-4

SECTION 6-6

SECTION 8-8

SECTION 10-10

SECTION 12-12

SECTION 14-14

SECTION 16-16

SECTION 18-18

SECTION 20-20

SECTION 22-22

SECTION 24-24

SECTION 26-26

SECTION 28-28

SECTION A-A

ARTERIAL DEVICE, SYSTEM AND METHOD FOR REMOVING EMBOLIC DEBRIS

FIELD OF THE INVENTION

This invention relates to arterial devices, systems and methods, particularly associated with performing cardiopulmonary bypass or the like, and/or associated with the removal of embolic debris.

BACKGROUND OF THE INVENTION

It is known that patients undergoing cardiopulmonary bypass (CPB) during cardiac surgery (usually open heart surgery (in which the heart is opened with a cutting instrument), but sometimes also closed heart surgery (in which the heart is not opened with a cutting instrument)) run a risk of neurologic and neuropsychologic deficit, which are thought to be caused or exacerbated by some types of embolic debris that are known to be released into the aortic arch during cardiac surgery or CPB and are introduced into the cerebral circulation.

Various devices, systems and methods are known for use in CPB. For example, U.S. Pat. No. 6,689,149 discloses a balloon occlusion device for aspirating embolic material from a blood vessel, such as from the aorta during cardiac surgery. The device includes an arterial cannula having a proximal end adapted to receive blood from a bypass-oxygenator machine, a distal end adapted to enter an artery, and a blood flow lumen extending between the proximal end and an outlet on the distal end. The cannula has an aspiration port proximate to the outlet, which communicates with an aspiration lumen. The cannula also includes an inflatable balloon attached to the cannula between the outlet and the aspiration port and capable of assuming an inflated condition for occluding a blood vessel. To use the device, the distal end of the cannula is introduced into a blood vessel, such as the aorta, the outlet is oriented downstream for delivering blood, and the balloon is inflated to occlude the vessel. In operation, fluid may then be flushed into and aspirated out through the aspiration port to remove loose embolic material from the vessel upstream of the balloon. Optionally, the device may include a second deployable balloon for further occluding the vessel at a second location.

U.S. Pat. No. 6,726,651 discloses methods, systems and devices for performing cardiopulmonary bypass (CPB), cardioplegic arrest, suction of fluid from the aorta to remove embolic or other fluid from the general circulation and the selective segmentation of the arterial system to perform differential perfusion eliminating hypoperfusion. An aortic catheter having an arch lumen which extends at least in part along the length of the catheter shaft has a proximal opening coupled to a CPB machine and a distal arch opening. A corporeal lumen extends at least in part along the length of the catheter shaft and has a proximal opening coupled to a CPB machine and a distal corporeal opening. A suction lumen extends at least in part along the length of the catheter shaft and has a proximal suction opening coupled to a suction source and a distal suction opening residing in the aortic lumen of a patient.

U.S. Pat. No. 5,697,905 discloses a method and apparatus used during cardiac surgery for reducing release of embolized air and particulate matter into general body circulatory system are disclosed. The method uses a catheter apparatus having an inflation lumen, an occlusive balloon, a suction lumen and a perfusion lumen. The catheter is inserted or navigated to into an aortic root and positioned so a suction opening communicates upstream of the aortic root and a perfusion opening communicates downstream of the suction opening. The patient's heart is stopped and the occlusive balloon is inflated to occlude the aorta. Cardiac surgery is performed and when the patient's heart is restarted the blood pumped by the heart during its first few contractions is suctioned through the suction opening.

U.S. Pat. No. 7,470,363 discloses a number of ultrasonic devices for preventing microbubbles and/or microparticles from reaching the brain during a percutaneous cardiological intervention (PCI) or cardiac surgery.

U.S. Pat. No. 5,425,724 discloses an aortic cannula having one tube for blood perfusion, and another tube for monitoring arterial pressure.

SUMMARY OF THE INVENTION

Embolic debris herein refers to any emboli or particles, including for example microparticles or microbubbles, that may be released as a result of the use of an artificial heart-lung machine (bypass-oxygenator machine), and/or due to clamping and/or manipulation of the aorta or the heart during CPB, for example. Embolic debris herein refers also to air bubbles, for example, as may exist in the heart ventricles prior to unclamping, and which are often released to the aorta after unclamping.

According to a first aspect of the invention there is provided an arterial system, comprising an arterial flow exchange system and a controller, for use with a patient having an aorta and a body blood circulation system, wherein:

said arterial flow exchange system comprises a distal portion arrangement configured for being accommodated in the aorta of the patient in use of the arterial flow exchange system, said distal portion arrangement comprising:

a perfusion lumen arrangement having at least one perfusion outlet and connectable to at least one perfusion source, said perfusion lumen arrangement being configured for providing therethrough a target perfusion flow into the aorta (via said at least one perfusion outlet) having a target perfusion flow rate that is greater than a nominal perfusion flow rate by an excess perfusion flow rate, wherein said nominal perfusion flow is sufficient for providing adequate fluid flow to the body blood circulation system of the patient; and a suction lumen arrangement having at least one suction inlet and connectable to a suction source, said suction lumen arrangement being configured for providing a suction flow out of the aorta (via said at least one suction inlet), said suction flow having a suction flow rate;

said distal portion being configured for providing fluid communication between at least one said perfusion outlet and at least one said suction inlet within the aorta via an outside of said distal portion, in use of the arterial system;

said controller being configured, in use of the arterial system, for:

selectively controllably providing a target perfusion flow into the aorta at said target perfusion flow rate;

selectively controllably providing a suction flow out of the aorta at said suction flow rate; and selectively controlling said target perfusion flow rate and said suction flow rate concurrently to cause embolic debris that may be present in the aorta to be diverted to said at least one suction inlet.

The arterial system according to this aspect of the invention may comprise any one of the following features, or more than one of the following features in any combination or permutation:

(A) wherein said controller is configured for selectively controlling said target perfusion flow rate and said suction flow rate to establish a recirculation flowfield between at least one said perfusion outlet and at least one said suction inlet within the aorta to cause the embolic debris that may be present in the aorta to be diverted to the respective at least one said suction inlet.

(B) wherein said controller is configured for selectively matching said suction flow rate with said excess perfusion flow rate according to a desired matching level, defined as a percentage of said suction flow rate with respect to said excess perfusion flow rate. For example, said matching level may be about 100%, or may be greater than 100%. For example, said matching level may be in a range between about 50% and about 100%.

(C) wherein said target perfusion flow rate is a first proportion of said nominal perfusion flow rate, wherein said first proportion is not less than about 110% of said nominal perfusion flow rate. For example, said first proportion may be between about 110% and about 150% of said nominal perfusion flow rate, or, for example, said first proportion may be between about 115% and about 160% of said nominal perfusion flow rate, or, for example, said first proportion may be between about 120% and about 150% of said nominal perfusion flow rate, or, for example, said first proportion may be between about 120% and about 170% of said nominal perfusion flow rate.

(D) wherein said suction flow rate is a second proportion of a said nominal perfusion flow rate, wherein said second proportion is not less than about 10% of said nominal perfusion flow rate. For example, said second proportion may be between about 10% and about 50% of said nominal perfusion flow rate, or, for example, said second proportion may be between about 15% and about 60% of said nominal perfusion flow rate, or, for example, said second proportion may be between about 20% and about 50% of said nominal perfusion flow rate, or, for example, said second proportion may be between about 20% and about 70% of said nominal perfusion flow rate.

(E) wherein said arterial flow exchange system is configured for operating in the aorta to provide said excess perfusion flow rate and to provide said suction flow rate in the absence of establishing occlusion of the aorta at least in a region of the aorta corresponding to a part of the arterial flow exchange system extending between said at least one suction inlet and said at least one perfusion outlet.

(F) wherein said device has an absence of an occlusion arrangement that is otherwise configured for providing occlusion of the aorta in operation of said system, at least between said at least one suction inlet and said at least one perfusion outlet.

(G) wherein said arterial system is configured for providing at least one said suction inlet within the ascending aorta of the patient in operation of the arterial system.

(H) wherein said arterial flow exchange system is configured in operation of the arterial system for causing at least a majority of embolic debris that may be present in the aorta to be diverted to said at least one suction inlet at least from upstream of said at least one suction inlet.

(I) wherein said controller is configured for providing said target perfusion flow rate wherein a corresponding target perfusion flow velocity is below a threshold value for avoiding or minimizing damage to blood cells, and/or, wherein said controller is configured for providing said suction flow rate at a corresponding suction flow velocity that is below a threshold value for avoiding or minimizing damage to blood cells; and/or wherein said perfusion lumen arrangement is configured for providing said target perfusion flow rate wherein a corresponding target perfusion flow velocity is below a threshold value for avoiding or minimizing damage to blood cells, and/or, wherein said suction lumen arrangement is configured for providing said suction flow rate at a corresponding suction flow velocity that is below a threshold value for avoiding or minimizing damage to blood cells.

(J) wherein said distal portion arrangement comprises at least one additional suction outlet port configured for de-airing the aorta by facilitating removing of said embolic debris in the form of air bubbles.

In at least a first form of the arterial system according to the first aspect of the invention, said arterial flow exchange system (as defined above, optionally comprising any one of features (A) to (J), or more than one of features (A) to (J) in any combination or permutation), may be embodied (in particular, may be integrally embodied) in an arterial device, and said distal portion arrangement constitutes a distal portion of said arterial device and is configured for being accommodated into the aorta.

In at least some embodiments according to the said first form of the arterial system, said arterial device is in the form of an aortic cannula, wherein said distal portion is configured for being introduced into the aorta via a wall of the ascending aorta. In at least one such embodiment, said distal portion comprises a curved portion and a distal end, wherein said distal end comprises said at least one perfusion outlet, and wherein said curved portion comprises said at least one suction inlet. In operation said at least one perfusion outlet is facing in a generally downstream direction along the aorta and said at least one suction inlet is facing in a generally upstream direction along the aorta. Optionally, said perfusion lumen arrangement comprises a first lumen, wherein said suction lumen arrangement comprises a second lumen, and wherein said first lumen and said second lumen are integrally formed in said distal portion. The first lumen may have a first flow cross-section and said second lumen may have a second flow cross-section, wherein a cross section ratio between said first flow cross-section and said second flow cross-section is not less than about 1.10. For example, said cross section ratio may be between about 1.10 and about 10.0. In at least some embodiments, said distal portion comprises one said perfusion outlet and one said suction inlet.

In at least some other embodiments according to the said first form of the arterial system, said arterial device is in the form of an aortic catheter, wherein said distal portion is configured for being introduced into the aorta via an entry point at a location downstream of the descending aorta, the distal portion being further configured for being navigated upstream to the ascending aorta. In at least one such embodiment, said distal portion comprises a distal end and an elongate portion extending proximally from said distal end, wherein said distal end comprises said at least one perfusion outlet, and wherein said elongate portion comprises said at least one suction inlet. In operation said at least one perfusion outlet is downstream of said at least one suction inlet with respect to antegrade flow in the aorta. In operation, said at least one suction inlet is facing in a generally upstream direction along the aorta in operation of the arterial system.

Optionally, said perfusion lumen arrangement comprises a first lumen and said suction lumen arrangement comprises a second lumen, and wherein said first lumen and said second lumen are integrally formed coaxially in said distal portion. Said first lumen may have a first flow cross-section and said second lumen may have a second flow cross-section, wherein a cross section ratio between said first flow cross-section and said second flow cross-section is not less than about 1.10. For example, said cross section ratio is between about 1.10 and about 10. In some such embodiments, said distal portion comprises a plurality of said perfusion outlets and one said suction inlet; in other such embodiments, said distal portion comprises a plurality of said perfusion outlets and a plurality of said suction inlets; optionally in either case, said plurality of perfusion outlet ports may comprise at least a first group of said perfusion outlet ports and a second group of said perfusion outlet ports, wherein said second group is located proximally of said first group, and wherein said first group is located within the ascending aorta or aortic arch in operation of the arterial system.

In at least a second form of the arterial system, said arterial flow exchange system (as defined above, optionally comprising any one of features (A) to (J), or more than one of features (A) to (J) in any combination or permutation), comprises a first arterial device and a second arterial device separate from said first arterial device, and said distal portion arrangement comprises a distal portion of said first arterial device and a distal portion of said second device, wherein said first arterial device and said second arterial device are configured for being independently accommodated into the aorta, wherein said perfusion lumen arrangement comprises at least a first perfusion lumen comprised in said first arterial device, and at least one second perfusion lumen comprised in said second arterial device, and wherein said suction lumen arrangement comprises at least one suction lumen comprised in said second arterial device.

In at least some embodiments following said second form of the arterial system said first arterial device is configured for providing said nominal perfusion flow rate via said at least one first perfusion lumen and at least one respective said perfusion outlet comprised in said first arterial device, wherein said second arterial device is configured for providing said excess perfusion flow rate via said at least one second perfusion lumen and at least one respective said perfusion outlet comprised in said second arterial device, and wherein said second arterial device is further configured to provide said suction flow rate via said suction lumen and at least one said suction inlet comprised in said second arterial device. In at least some such embodiments, said second arterial device is in the form of an aortic cannula, wherein said second distal portion is configured for being introduced into the aorta via a wall of the ascending aorta. Additionally or alternatively, (i) said first arterial device is in the form of an aortic cannula, wherein said first distal portion is configured for being introduced into the aorta via a wall of the aorta proximal to said second arterial device, or (ii) said first arterial device is in the form of an aortic catheter, wherein said first distal portion is configured for being introduced into the aorta via an entry point at a location downstream of the descending aorta, the first distal portion being further configured for being navigated upstream to the ascending aorta to a position proximal to said second arterial device.

According to the first aspect of the invention, the arterial system, as defined above, optionally comprising any one of features (A) to (J), or more than one of features (A) to (J) in any combination or permutation, and/or according to the aforementioned first form of the arterial system or according to the aforementioned second form of the arterial system, may be further configured according to any one of the following features, or according to more than one of the following features in any combination or permutation:

- (K) wherein said nominal perfusion flow rate is in the range between about 3 liters per minute to about 5 liters per minute;
- (L) wherein said target flow rate is in the range between about 3.3 liters per minute to about 7.5 liters per minute;
- (M) wherein said excess perfusion flow rate is in the range between about 0.3 liters per minute to about 2.5 liters per minute;
- (N) wherein said suction flow rate is greater than 0.5 liters per minute;
- (O) wherein said suction flow rate is greater than 0.75 liters per minute; wherein said suction flow rate is greater than 1 liter per minute;
- (P) wherein said suction flow rate is greater than 1.25 liters per minute;
- (Q) wherein said suction flow rate is in the range between about 0.5 liters per minute to about 2.0 liters per minute;
- (R) wherein said suction flow rate is in the range between about 0.5 liters per minute to about 2.5 liters per minute;
- (S) wherein said suction flow rate is in the range between about 0.75 liters per minute to about 2.5 liters per minute.

In operation of the arterial system according to the first aspect of the invention, said perfusion lumen arrangement is connected to said at least one perfusion source, and said suction lumen arrangement is connected to said suction source.

According to the first aspect of the invention there is also provided an arterial device, for use with a patient having an aorta and a body blood circulation system, the arterial device comprising a distal portion arrangement configured for being accommodated in the aorta of the patient in use of the arterial device, said distal portion arrangement comprising:

- a perfusion lumen arrangement having at least one perfusion outlet and connectable to at least one perfusion source, said perfusion lumen arrangement being configured for providing therethrough a target perfusion flow into the aorta (via said at least one perfusion outlet) having a target perfusion flow rate that is greater than a nominal perfusion flow rate by an excess perfusion flow rate, wherein said nominal perfusion flow is sufficient for providing adequate fluid flow to the body blood circulation system of the patient; and
- a suction lumen arrangement having at least one suction inlet and connectable to a suction source, said suction lumen arrangement being configured for providing a suction flow out of the aorta (via said at least one suction inlet), said suction flow having a suction flow rate;
- said distal portion being configured for providing fluid communication between at least one said perfusion outlet and at least one said suction inlet within the aorta via an outside of said distal portion, in use of the arterial device;
- wherein the arterial device is configured for enabling said target perfusion flow rate and said suction flow rate to be concurrently and selectively controlled to cause embolic debris that may be present in the aorta to be diverted to said at least one suction inlet.

The arterial device according to this aspect of the invention and as defined above may comprise any one of the following features, or more than one of the following features in any combination or permutation:

(A1) wherein said arterial device is configured for enabling selectively matching said suction flow rate with said excess perfusion flow rate according to a desired matching level, defined as a percentage of said suction flow rate with respect to said excess perfusion flow rate. For example, said matching level may be about 100%, or may be greater than 100%. For example, said matching level may be in a range between about 50% and about 100%.

(B1) wherein said target perfusion flow rate is a first proportion of said nominal perfusion flow rate, wherein said first proportion is not less than about 110% of said nominal perfusion flow rate. For example, said first proportion may be between about 110% and about 150% of said nominal perfusion flow rate, or, for example, said first proportion may be between about 115% and about 160% of said nominal perfusion flow rate, or, for example, said first proportion may be between about 120% and about 150% of said nominal perfusion flow rate, or, for example, said first proportion may be between about 120% and about 170% of said nominal perfusion flow rate.

(C1) wherein said suction flow rate is a second proportion of a said nominal perfusion flow rate, wherein said second proportion is not less than about 10% of said nominal perfusion flow rate. For example, said second proportion may be between about 10% and about 50% of said nominal perfusion flow rate, or, for example, said second proportion may be between about 15% and about 60% of said nominal perfusion flow rate, or, for example, said second proportion may be between about 20% and about 50% of said nominal perfusion flow rate, or, for example, said second proportion may be between about 20% and about 70% of said nominal perfusion flow rate.

(D1) wherein said arterial device is configured for operating in the aorta to provide said excess perfusion flow rate and to provide said suction flow rate in the absence of establishing occlusion of the aorta at least in a region of the aorta corresponding to a part of the arterial device extending between said at least one suction inlet and said at least one perfusion outlet.

(E1) wherein said device having an absence of an occlusion arrangement that is otherwise configured for providing occlusion of the aorta in operation of said arterial device, at least between said at least one suction inlet and said at least one perfusion outlet.

(F1) wherein said arterial device is configured for providing at least one said suction inlet within the ascending aorta of the patient in operation of the arterial device.

(G1) wherein said flow exchange arterial device is configured in operation of the arterial device for causing at least a majority of embolic debris that may be present in the aorta to be diverted to said at least one suction inlet at least from upstream of said at least one suction inlet.

(H1) wherein said arterial device is configured for providing said target perfusion flow rate wherein a corresponding target perfusion flow velocity is below a threshold value for avoiding or minimizing damage to blood cells, and/or wherein said arterial device is configured for providing said suction flow rate at a corresponding suction flow velocity that is below a threshold value for avoiding or minimizing damage to blood cells; and/or wherein said perfusion lumen arrangement is configured for providing said target perfusion flow rate wherein a corresponding target perfusion flow velocity is below a threshold value for avoiding or minimizing damage to blood cells, and/or, wherein said suction lumen arrangement is configured for providing said suction flow rate at a corresponding suction flow velocity that is below a threshold value for avoiding or minimizing damage to blood cells.

(I1) wherein said distal portion arrangement comprises at least one additional suction outlet port configured for de-airing the aorta by facilitating removing of said embolic debris in the form of air bubbles.

In at least a first group of embodiments, said arterial device as defined above, optionally comprising any one of features (A1) to (I1), or more than one of features (A1) to (I1) in any combination or permutation, is in the form of an aortic cannula, wherein said distal portion is configured for being introduced into the aorta via a wall of the ascending aorta. In at least one such embodiment of said first group, said distal portion comprises a curved portion and a distal end, wherein said distal end comprises said at least one perfusion outlet, and wherein said curved portion comprises said at least one suction inlet. In operation said at least one perfusion outlet is facing in a generally downstream direction along the aorta and said at least one suction inlet is facing in a generally upstream direction along the aorta. Additionally or alternatively, said perfusion lumen arrangement comprises a first lumen, wherein said suction lumen arrangement comprises a second lumen, and wherein said first lumen and said second lumen are integrally formed in said distal portion. The first lumen may have a first flow cross-section and said second lumen may have a second flow cross-section, wherein a cross section ratio between said first flow cross-section and said second flow cross-section is not less than about 1.10. For example, said cross section ratio is between about 1.10 and about 10.0. In at least some such embodiments of said first group, said distal portion comprises one said perfusion outlet and one said suction inlet.

In at least a second group of embodiments, said arterial device as defined above, optionally comprising any one of features (A1) to (I1), or more than one of features (A1) to (I1) in any combination or permutation, is in the form of an aortic catheter, wherein said distal portion is configured for being introduced into the aorta via an entry point at a location downstream of the descending aorta, the distal portion being further configured for being navigated upstream to the ascending aorta. In at least some such embodiments of said second group, said distal portion comprises a distal end and an elongate portion extending proximally from said distal end, wherein said distal end comprises said at least one perfusion outlet, and wherein said elongate portion comprises said at least one suction inlet. In operation said at least one perfusion outlet is downstream of said at least one suction inlet with respect to antegrade flow in the aorta. In at least some such embodiments of said second group of embodiments, said at least one suction inlet is facing in a generally upstream direction along the aorta in operation of the arterial device. Optionally, said perfusion lumen arrangement comprises a first lumen and said suction lumen arrangement comprises a second lumen, and wherein said first lumen and said second lumen are integrally formed coaxially in said distal portion. Said first lumen may have a first flow cross-section and said second lumen may have a second flow cross-section, wherein a cross section ratio between said first flow cross-section and said second flow cross-section is not less than about 1.10. For example, said cross section ratio is between about 1.10 and about 10. In some such embodiments, said distal portion comprises a plurality of said perfusion outlets and one said suction inlet; in other such embodiments, said distal portion comprises a plurality of said perfusion outlets and a plurality of said suction inlets; optionally in either case, said plurality of perfusion outlet ports comprises at least a first group of said perfusion outlet ports and a second group of said perfusion outlet ports, wherein said second group of said perfusion outlet ports is located proximally of said first group of said perfusion outlet ports, and wherein said first group of said perfusion outlet ports is located within the ascending aorta or aortic arch in operation of the arterial device.

According to the first aspect of the invention, the arterial device, as defined above, optionally comprising any one of features (A1) to (I1), or more than one of features (A1) to (I1) in any combination or permutation, and/or according to the aforementioned first group of embodiments of the arterial device or according to the aforementioned second group of embodiments of the arterial device, may be further configured according to any one of the following features, or according to more than one of the following features in any combination or permutation:

- (J1) wherein said nominal perfusion flow rate is in the range between about 3 liters per minute to about 5 liters per minute;
- (K1) wherein said target flow rate is in the range between about 3.3 liters per minute to about 7.5 liters per minute;
- (L1) wherein said excess perfusion flow rate is in the range between about 0.3 liters per minute to about 2.5 liters per minute;
- (M1) wherein said suction flow rate is greater than 0.5 liters per minute;
- (N1) wherein said suction flow rate is greater than 0.75 liters per minute; wherein said suction flow rate is greater than 1 liter per minute;
- (O1) wherein said suction flow rate is greater than 1.25 liters per minute;
- (P1) wherein said suction flow rate is in the range between about 0.5 liters per minute to about 2.0 liters per minute;
- (Q1) wherein said suction flow rate is in the range between about 0.5 liters per minute to about 2.5 liters per minute;
- (R1) wherein said suction flow rate is in the range between about 0.75 liters per minute to about 2.5 liters per minute.

According to the first aspect of the invention there is also provided a method for removing embolic debris from an aorta of a patient having a body blood circulation system, comprising:

- (a) providing an arterial flow exchange system comprising a distal portion arrangement configured for being accommodated in the aorta of the patient in use of the arterial flow exchange system, said distal portion arrangement comprising:
  a perfusion lumen arrangement having at least one perfusion outlet and connectable to at least one perfusion source, said perfusion lumen arrangement being configured for providing therethrough a target perfusion flow into the aorta having a target perfusion flow rate that is greater than a nominal perfusion flow rate by an excess perfusion flow rate, wherein said nominal perfusion flow is sufficient for providing adequate fluid flow to the body blood circulation system of the patient; and
  a suction lumen arrangement having at least one suction inlet and connectable to a suction source, said suction lumen arrangement being configured for providing a suction flow out of the aorta, said suction flow having a suction flow rate;
  said distal portion being configured for providing fluid communication between at least one said perfusion outlet and at least one said suction inlet within the aorta via an outside of said distal portion, in use of the arterial flow exchange system;
- (b) accommodating said distal portion arrangement in the aorta of the patient so that at least one said suction inlet port is accommodated in the ascending aorta of the patient;
- (c) controllably providing a target perfusion flow into the aorta at said target perfusion flow rate;
- (d) controllably providing a suction flow out of the aorta at said suction flow rate; and
- (e) selectively controlling said target perfusion flow rate and said suction flow rate to cause embolic debris that may be present in the aorta to be diverted to said at least one suction inlet.

Optionally, step (e) comprises selectively controlling said target perfusion flow rate and said suction flow rate to establish a recirculation flowfield between at least one said perfusion outlet and at least one said suction inlet within the aorta to cause the embolic debris that may be present in the aorta to be diverted to the respective at least one said suction inlet.

Additionally or alternatively, step (b) comprises accommodating said distal portion arrangement in the aorta of the patient so that at least one said perfusion outlet port is accommodated in the ascending aorta of the patient.

Additionally or alternatively, step (b) comprises accommodating said distal portion arrangement in the aorta of the patient so that at least one said perfusion outlet port is accommodated in the aortic arch of the patient.

Additionally or alternatively, step (e) comprises selectively matching said suction flow rate with said excess perfusion flow rate according to a desired matching level, defined as a percentage of said suction flow rate with respect to said excess perfusion flow rate. For example, said matching level is about 100%, or above 100%. For example, said matching level is between about 50% and about 100%.

Additionally or alternatively, said target perfusion flow rate is a first proportion of said nominal perfusion flow rate, wherein said first proportion is not less than about 110% of said nominal perfusion flow rate.

Additionally or alternatively, said target perfusion flow rate is a first proportion of said nominal perfusion flow rate, wherein said first proportion is not less than about 110% of said nominal perfusion flow rate. For example, said first proportion may be between about 110% and about 150% of said nominal perfusion flow rate, or, for example, said first proportion may be between about 115% and about 160% of said nominal perfusion flow rate, or, for example, said first proportion may be between about 120% and about 150% of said nominal perfusion flow rate, or, for example, said first proportion may be between about 120% and about 170% of said nominal perfusion flow rate.

Additionally or alternatively, said suction flow rate is a second proportion of a said nominal perfusion flow rate, wherein said second proportion is not less than about 10% of said nominal perfusion flow rate. For example, said second proportion may be between about 10% and about 50% of said nominal perfusion flow rate, or, for example, said second proportion may be between about 15% and about 60% of said nominal perfusion flow rate, or, for example, said second proportion may be between about 20% and about 50% of said nominal perfusion flow rate, or, for example, said second proportion may be between about 20% and about 70% of said nominal perfusion flow rate.

Additionally or alternatively, said, at least steps (b) to (e) are conducted in the absence of establishing occlusion of the aorta at least in a region of the aorta corresponding to a part of the device extending between said at least one suction inlet and said at least one perfusion outlet.

Additionally or alternatively, said device has an absence of an occlusion arrangement that is otherwise configured for providing occlusion of the aorta in operation of said device, at least between said at least one suction inlet and said at least one perfusion outlet.

Additionally or alternatively, in step (e) at least a majority of embolic debris that may be present in the aorta are caused to be diverted to said at least one suction inlet at least from upstream of said at least one suction inlet.

Additionally or alternatively, said target perfusion flow rate is provided having a corresponding target perfusion flow velocity that is below a threshold value for avoiding or minimizing damage to blood cells, and/or said suction flow rate is provided at a corresponding suction flow velocity that is below a threshold value for avoiding or minimizing damage to blood cells.

Additionally or alternatively, said distal portion arrangement comprises at least one additional suction outlet port configured for de-airing the aorta, and further comprising the step of removing said embolic debris in the form of air bubbles.

In at least a first form of carrying out the method, said arterial flow exchange system is embodied in an arterial device, and said distal portion arrangement constitutes a distal portion of said arterial device and configured for being accommodated into the aorta.

For example, said arterial device is in the form of an aortic cannula, and in step (b) said distal portion is introduced into the aorta via a wall of the ascending aorta.

Alternatively, said arterial device is in the form of an aortic catheter, and in step (b) said distal portion is introduced into the aorta via an entry point at a location downstream of the descending aorta, and said distal portion is navigated upstream to the ascending aorta. For example, said entry point is provided in a femoral artery or an iliac artery of the patient.

Additionally or alternatively, said perfusion lumen arrangement comprises a perfusion lumen having a first flow cross-section, and said suction lumen arrangement comprises a suction lumen having a second flow cross-section, wherein a cross section ratio between said first flow cross-section and said second flow cross-section is not less than about 1.10. For example, said cross section ratio is between about 1.10 and about 1.5.

In at least a second form of carrying out the method, said arterial flow exchange system comprises a first arterial device and a second arterial device separate from said first arterial device, and said distal portion arrangement comprises a distal portion of said first arterial device and a distal portion of said second device, wherein said first arterial device and said second arterial device are independently accommodated into the aorta, wherein said perfusion lumen arrangement comprises at least a first perfusion lumen comprised in said first arterial device, and at least one second perfusion lumen comprised in said second arterial device, and wherein said suction lumen arrangement comprises at least one suction lumen comprised in said second arterial device. For example, said first arterial device is operated to provide said nominal perfusion flow rate via said at least one first perfusion lumen and at least one respective said perfusion outlet comprised in said first arterial device, wherein said second arterial device is operated to provide said excess perfusion flow rate via said at least one second perfusion lumen and at least one respective said perfusion outlet comprised in said second arterial device, and wherein said second arterial device is further operated to provide said suction flow rate via said suction lumen and at least one said suction inlet comprised in said second arterial device.

According to the first aspect of the invention, the method for removing embolic debris from an aorta of a patient having a body blood circulation system, may further comprise one or more of the following features in any combination or permutation:

wherein said nominal perfusion flow rate is provided in the range between about 3 liters per minute to about 5 liters per minute;

wherein said target flow rate is provided in the range between about 3.3 liters per minute to about 7.5 liters per minute;

wherein said excess perfusion flow rate is provided in the range between about 0.3 liters per minute to about 2.5 liters per minute;

wherein said suction flow rate is greater than 0.5 liters per minute; r wherein said suction flow rate is greater than 0.75 liters per minute; wherein said suction flow rate is greater than 1 liter per minute;

wherein said suction flow rate is greater than 1.25 liters per minute;

wherein said suction flow rate is in the range between about 0.5 liters per minute to about 2.0 liters per minute;

wherein said suction flow rate is in the range between about 0.5 liters per minute to about 2.5 liters per minute;

wherein said suction flow rate is in the range between about 0.75 liters per minute to about 2.5 liters per minute.

According to a second aspect of the invention there is provided an arterial device, for use with a patient having an aorta and a body blood circulation system, the arterial device comprising a distal portion arrangement configured for being accommodated in the aorta of the patient in use of the system, said distal portion arrangement comprising:

a perfusion lumen arrangement having at least one perfusion outlet and connectable to at least one perfusion source, wherein said perfusion lumen arrangement is configured for providing therethrough a perfusion flow into the aorta (via said at least one perfusion outlet), said perfusion flow having a perfusion flow rate; and a suction lumen arrangement having at least one suction inlet and connectable to a suction source, said suction lumen arrangement being configured for providing a suction flow out of the aorta (via said at least one suction inlet), said suction flow having a suction flow rate;

wherein said suction flow rate is greater than 0.5 liters per minute.

The arterial device according to the second aspect of the invention may comprise any one of the following features (a2) to (d2), or more than one of the following features (a2) to (d2), in any combination or permutation:

(a2) wherein said suction lumen arrangement is configured for providing said suction flow rate at a corresponding suction flow velocity that is below a threshold value for avoiding or minimizing damage to blood cells.

(b2) wherein said perfusion flow rate comprises a target perfusion flow rate that is greater than a nominal perfusion flow rate by an excess perfusion flow rate, wherein said nominal perfusion flow is sufficient for providing adequate fluid flow to the body blood circulation system of the patient.

(c2) wherein said distal portion is configured for providing fluid communication between at least one said perfusion outlet and at least one said suction inlet within the aorta via an outside of said distal portion, in use of the arterial device.

(d2) wherein said distal portion is configured for providing fluid communication between at least one said perfusion outlet and at least one said suction inlet within the aorta via an outside of said distal portion, in use of the arterial device.

Furthermore, the arterial device according to the second aspect of the invention may comprise any one of the following features (A2) to (I2), or more than one of the following features (A2) to (I2), in any combination or permutation:

(A2) wherein said arterial device is configured for enabling selectively matching said suction flow rate with said excess perfusion flow rate according to a desired matching level, defined as a percentage of said suction flow rate with respect to said excess perfusion flow rate. For example, said matching level may be about 100%, or may be greater than 100%. For example, said matching level may be in a range between about 50% and about 100%.

(B2) wherein said target perfusion flow rate is a first proportion of said nominal perfusion flow rate, wherein said first proportion is not less than about 110% of said nominal perfusion flow rate. For example, said first proportion may be between about 110% and about 150% of said nominal perfusion flow rate, or, for example, said first proportion may be between about 115% and about 160% of said nominal perfusion flow rate, or, for example, said first proportion may be between about 120% and about 150% of said nominal perfusion flow rate, or, for example, said first proportion may be between about 120% and about 170% of said nominal perfusion flow rate.

(C2) wherein said suction flow rate is a second proportion of a said nominal perfusion flow rate, wherein said second proportion is not less than about 10% of said nominal perfusion flow rate. For example, said second proportion may be between about 10% and about 50% of said nominal perfusion flow rate, or, for example, said second proportion may be between about 15% and about 60% of said nominal perfusion flow rate, or, for example, said second proportion may be between about 20% and about 50% of said nominal perfusion flow rate, or, for example, said second proportion may be between about 20% and about 70% of said nominal perfusion flow rate.

(D2) wherein said arterial device is configured for operating in the aorta to provide said excess perfusion flow rate and to provide said suction flow rate in the absence of establishing occlusion of the aorta at least in a region of the aorta corresponding to a part of the arterial device extending between said at least one suction inlet and said at least one perfusion outlet.

(E2) wherein said device having an absence of an occlusion arrangement that is otherwise configured for providing occlusion of the aorta in operation of said arterial device, at least between said at least one suction inlet and said at least one perfusion outlet.

(F2) wherein said arterial device is configured for providing at least one said suction inlet within the ascending aorta of the patient in operation of the arterial device.

(G2) wherein said flow exchange arterial device is configured in operation of the arterial device for causing at least a majority of embolic debris that may be present in the aorta to be diverted to said at least one suction inlet at least from upstream of said at least one suction inlet.

(H2) wherein said arterial device is configured for providing said target perfusion flow rate wherein a corresponding target perfusion flow velocity is below a threshold value for avoiding or minimizing damage to blood cells.

(I2) wherein said distal portion arrangement comprises at least one additional suction outlet port configured for de-airing the aorta by facilitating removing of said embolic debris in the form of air bubbles.

In at least a first group of embodiments according to the second aspect of the invention, said arterial device, optionally comprising any one of features (a2) to (d2) or (A2) to (I2), or more than one of features (a2) to (d2) and/or (A2) to (I2) in any combination or permutation, is in the form of an aortic cannula, wherein said distal portion is configured for being introduced into the aorta via a wall of the ascending aorta. In at least one such embodiment of said first group, said distal portion comprises a curved portion and a distal end, wherein said distal end comprises said at least one perfusion outlet, and wherein said curved portion comprises said at least one suction inlet. In operation said at least one perfusion outlet is facing in a generally downstream direction along the aorta and said at least one suction inlet is facing in a generally upstream direction along the aorta. Additionally or alternatively, said perfusion lumen arrangement comprises a first lumen, wherein said suction lumen arrangement comprises a second lumen, and wherein said first lumen and said second lumen are integrally formed in said distal portion. The first lumen may have a first flow cross-section and said second lumen may have a second flow cross-section, wherein a cross section ratio between said first flow cross-section and said second flow cross-section is not less than about 1.10. For example, said cross section ratio is between about 1.10 and about 10.0. In at least some such embodiments of said first group, said distal portion comprises one said perfusion outlet and one said suction inlet.

In at least a second group of embodiments according to the second aspect of the invention, said arterial device, optionally comprising any one of features (a2) to (d2) or (A2) to (I2), or more than one of features (a2) to (d2) and/or (A2) to (I2) in any combination or permutation, is in the form of an aortic catheter, wherein said distal portion is configured for being introduced into the aorta via an entry point at a location downstream of the descending aorta, the distal portion being further configured for being navigated upstream to the ascending aorta. In at least some such embodiments of said second group, said distal portion comprises a distal end and an elongate portion extending proximally from said distal end, wherein said distal end comprises said at least one perfusion outlet, and wherein said elongate portion comprises said at least one suction inlet. In operation said at least one perfusion outlet is downstream of said at least one suction inlet with respect to antegrade flow in the aorta. In at least some such embodiments of said second group of embodiments, said at least one suction inlet is facing in a generally upstream direction along the aorta in operation of the arterial device. Optionally, said perfusion lumen arrangement comprises a first lumen and said suction lumen arrangement comprises a second lumen, and wherein said first lumen and said second lumen are integrally formed coaxially in said distal portion. Said first lumen may have a first flow cross-section and said second lumen may have a second flow cross-section, wherein a cross section ratio between said first flow cross-section and said second flow cross-section is not less than about 1.10. For example, said cross section ratio is between about 1.10 and about 10. In some such embodiments, said distal portion comprises a plurality of said perfusion outlets and one said suction inlet; in other such embodiments, said distal portion comprises a plurality of said perfusion outlets and a plurality of said suction inlets; optionally in either case, said plurality of perfusion outlet ports comprises at least a first group of said perfusion outlet ports and a second group of said perfusion outlet ports, wherein said second group of said perfusion outlet ports is located proximally of said first group of said perfusion outlet ports, and wherein said first group of said perfusion outlet ports is located within the ascending aorta or aortic arch in operation of the arterial device.

According to the second aspect of the invention, the arterial device, as defined above, optionally comprising any one of features (a2) to (d2) and/or (A2) to (I2), or more than one of features (a2) to (d2) and/or (A2) to (I2) in any combination or permutation, and/or according to the aforementioned first group of embodiments or according to the aforementioned second group of embodiments of the arterial device, may be further configured according to any one of the following features, or according to more than one of the following features in any combination or permutation:

(J2) wherein said nominal perfusion flow rate is in the range between about 3 liters per minute to about 5 liters per minute;

(K2) wherein said target flow rate is in the range between about 3.3 liters per minute to about 7.5 liters per minute;

(L2) wherein said excess perfusion flow rate is in the range between about 0.3 liters per minute to about 2.5 liters per minute;

(M2) wherein said suction flow rate is greater than 0.75 liters per minute; wherein said suction flow rate is greater than 1 liter per minute;

(N2) wherein said suction flow rate is greater than 1.25 liters per minute;

(O2) wherein said suction flow rate is in the range between about 0.5 liters per minute to about 2.0 liters per minute;

(P2) wherein said suction flow rate is in the range between about 0.5 liters per minute to about 2.5 liters per minute;

(Q2) wherein said suction flow rate is in the range between about 0.75 liters per minute to about 2.5 liters per minute.

According to the second aspect of the invention, there is also provided an arterial system for use with a patient having an aorta and a body blood circulation system, comprising:

an arterial device as defined herein according to the second aspect of the invention;

a controller, configured, in use of the arterial system, for:
selectively controllably providing a target perfusion flow into the aorta at said target perfusion flow rate;
selectively controllably providing a suction flow out of the aorta at said suction flow rate; and
selectively controlling said target perfusion flow rate and said suction flow rate concurrently to cause embolic debris that may be present in the aorta to be diverted to said at least one suction inlet.

In operation of the arterial system according to the second aspect of the invention, said perfusion lumen arrangement is connected to said at least one perfusion source, and said suction lumen arrangement is connected to said suction source.

According to the second aspect of the invention there is also provided a method for removing embolic debris from an aorta of a patient having a body blood circulation system, comprising:

providing an arterial device according to the second aspect of the invention;

accommodating a distal portion arrangement of the device in the aorta of the patient so that at least at least one said suction inlet port is accommodated in the ascending aorta of the patient;

controllably providing a suction flow out of the aorta at said suction flow rate, wherein said suction flow rate is greater than 0.5 liters per minute.

Additionally, the method may also comprise the following steps:

controllably providing a target perfusion flow into the aorta at said target perfusion flow rate; and selectively controlling said target perfusion flow rate and said suction flow rate to cause embolic debris that may be present in the aorta to be diverted to said at least one suction inlet.

According to at least some aspects of the invention, there is provided an arterial device, system and method are provided for use with a patient undergoing a cardiac procedure. The system is configured for enabling one or more arterial devices to be accommodated in the aorta of the patient in use of the system, and a perfusion lumen arrangement provides therethrough a target perfusion flow into the aorta having a target perfusion flow rate that is significantly greater than a nominal perfusion flow rate, by an excess perfusion flow rate. A suction lumen arrangement provides therethrough a suction flow out of the aorta at a suction flow rate. The target perfusion flow rate and the suction flow rate may be concurrently and selectively controlled to cause embolic debris that may be present in the aorta to be diverted to the suction inlet, while providing the nominal flow rate to the body circulation of the patient.

Herein, the term "distal" refers to a direction generally towards the inside of the body from an outside thereof, while the term "proximal" refers to a direction generally towards the outside of the body from an inside thereof.

Herein, "nominal perfusion flow" refers to a perfusion flow that is the minimum sufficient for providing adequate fluid flow to the body blood circulation system of the patient, i.e., a minimum perfusion flow having a corresponding nominal perfusion flow rate that is sufficient to sustain the full metabolic demands of the patient. In practice, a patient may have an actual perfusion flow rate, normally provided by the heart, that can vary within a range, and this range may change according to the respective condition of the patient, and depend on various factors that define this condition, for example including one or more of state of health, body temperature, body activity and so on. Thus, the nominal perfusion flow rate herein refers to the minimum perfusion flow rate of the range of perfusion flow rates for the respective condition of the patient. The nominal perfusion flow rate is in practice conventionally determined by the medical staff carrying out the respective cardiac procedure, and there are a number of standard conventional methods commonly used for determining the nominal perfusion flow rate for a particular patient. For example, one such method is based on body surface area (BSA), and a fixed perfusion flow rate per square meter of body surface of the patient is provided. This fixed perfusion flow rate per square meter of body surface of the patient may be, for example, about 2.4 liters per minute per square meter, and thus, for example, a patient having a BSA of 1.8 m$^2$ would have a nominal perfusion flow rate of about 4.3 liters/min (=2.4*1.8). In some cases, the fixed perfusion flow rate per square meter of body surface of the patient may be different from 2.4 liters per minute per square meter—for example 2.3 liters per minute per square meter, or 2.5 liters per minute per square meter. Other methods may be used for determining the nominal perfusion flow rate for the patient, for example employing known dynamic calculation that may change the nominal perfusion flow rate during the cardiac procedure.

The "body blood circulation system" of the patient herein includes the corporeal body circulation system and the cerebral circulation system which are normally supplied by the aorta.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
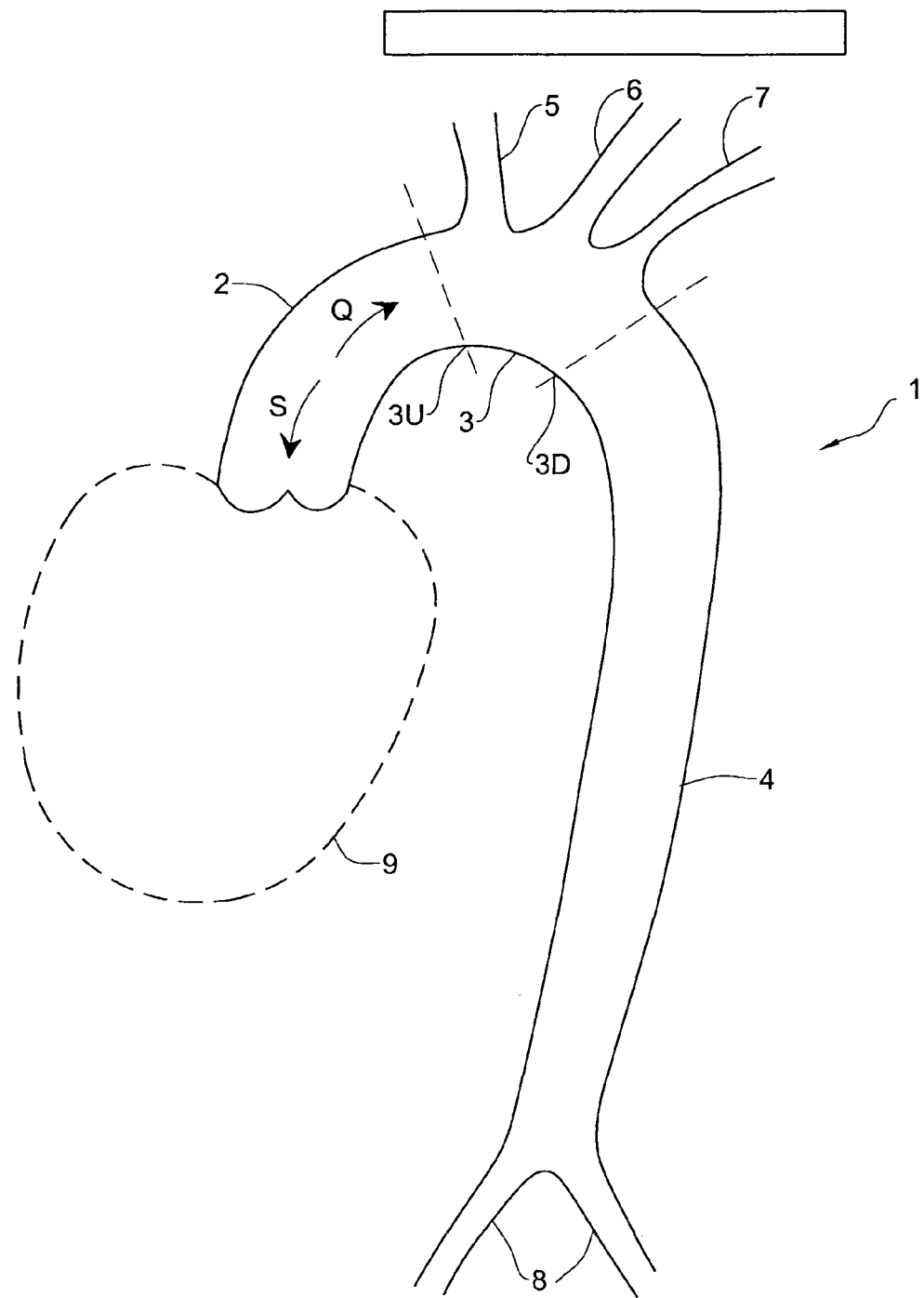
FIG. 1 is a simplified schematic illustration of the general anatomy of the aorta.

By way of general background, FIG. 1 illustrates schematically the anatomy of the aorta 1, which is the main blood conduit of a series of blood vessels which transport oxygenated blood from the heart to the body tissues of a patient. The aorta is, for ease of reference, divided into the following portions: the ascending aorta 2, the aortic arch 3, and the descending aorta 4. The ascending aorta 2 extends from the upper part of the left ventricle of the heart 9 to the upstream end 3U of the aortic arch 3. The aortic arch 3 has three branches—the innominate artery 5 (also referred to as brachiocephalic artery), the left common carotid artery 6 and the left subclavian artery 7—which supply oxygenated blood to the cerebral circulation system. The descending aorta 4 starts at the downstream end 3D of the aortic arch 3 and supplies oxygenated blood to the corporeal body circulation system. The descending aorta 4 continues through the abdomen and splits into the two common iliac arteries 8 that supply oxygenated blood to the lower extremities of the body.

Figure 2:
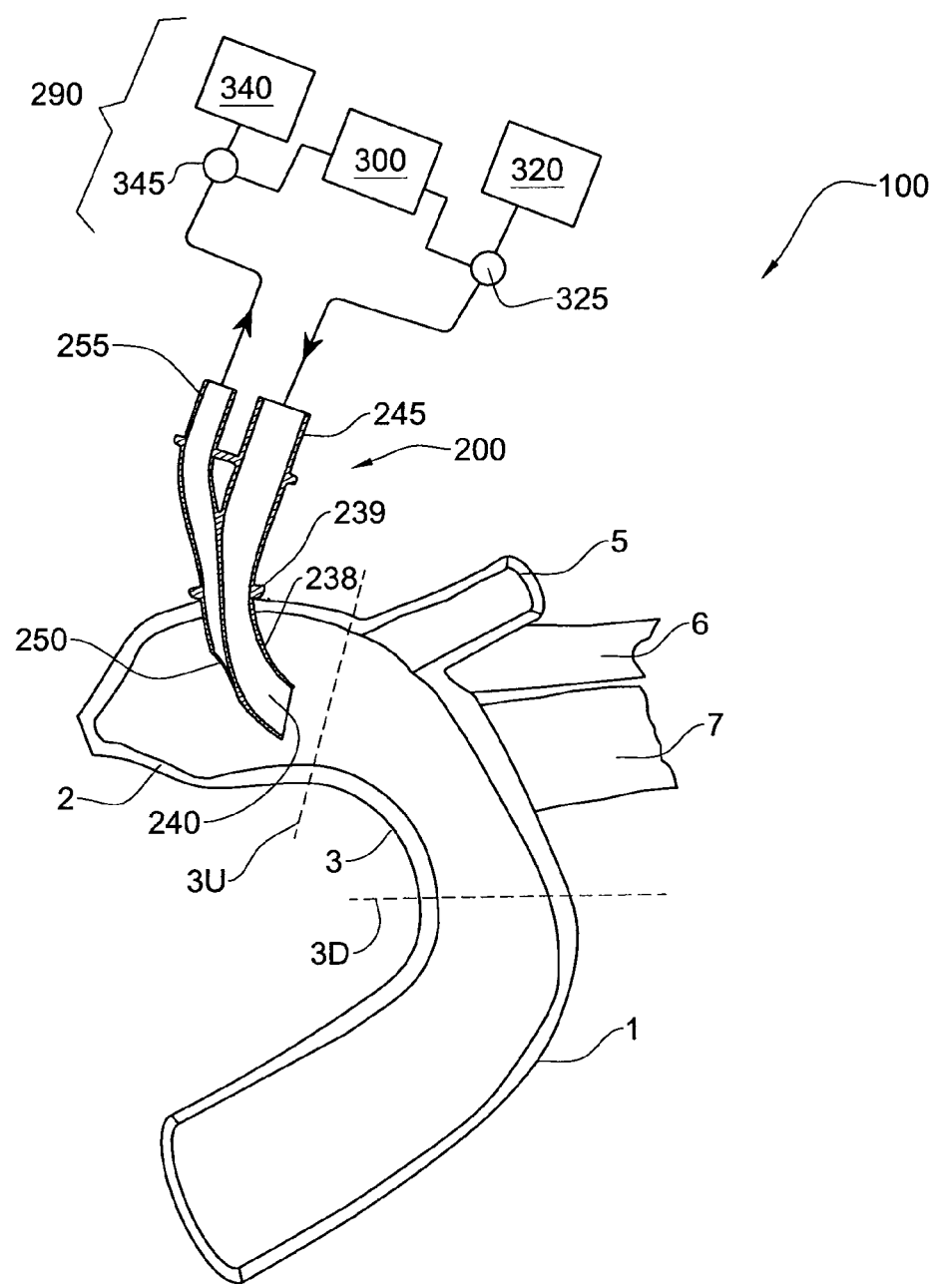
FIG. 2 is a schematic illustration of an aortic system according to a first embodiment of the invention, wherein the respective aortic device is installed in the aorta.
Figure 3:
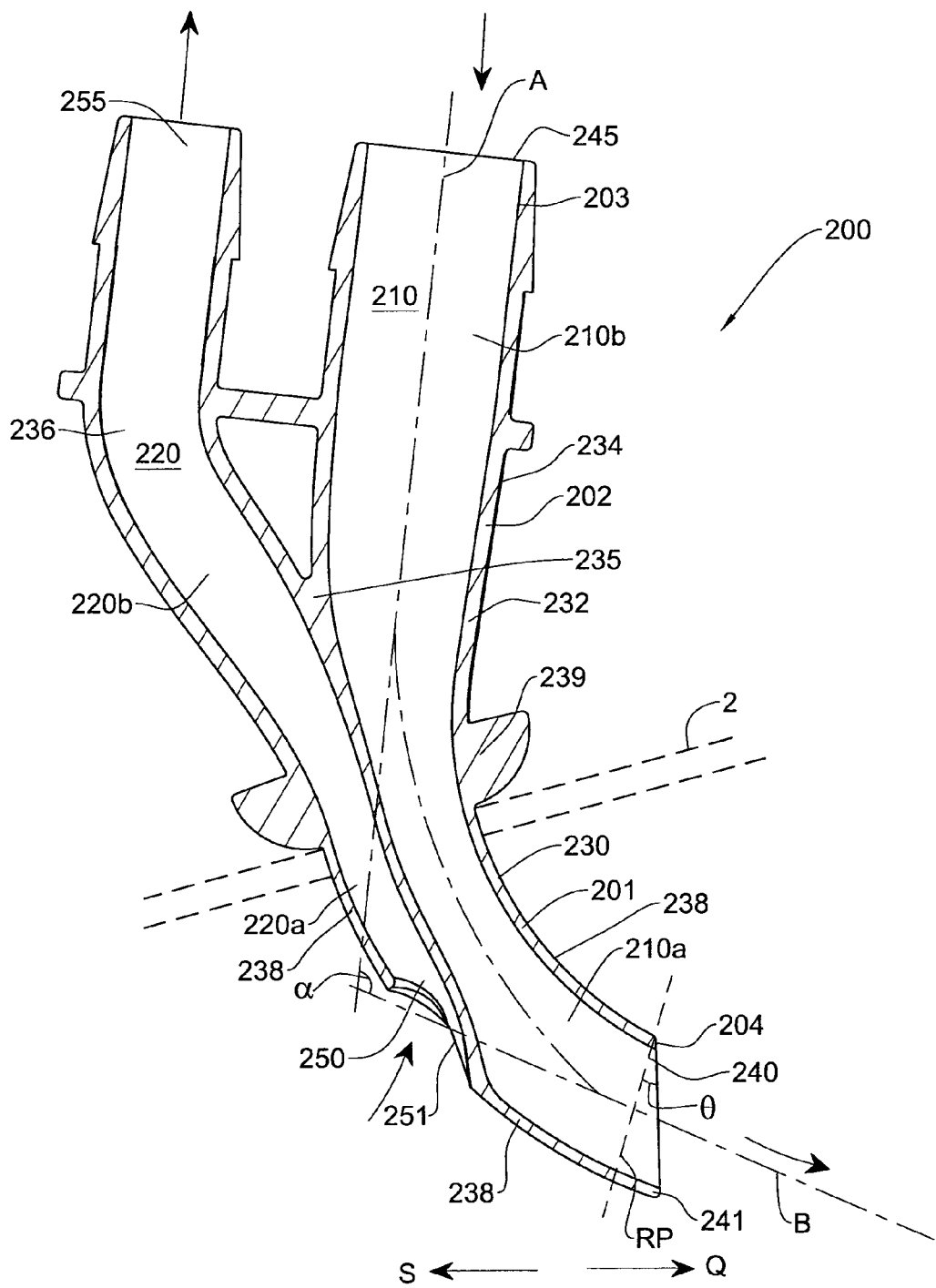
FIG. 3 is a cross-sectional side view of the aortic device of the embodiment of FIG. 2.

Referring to FIGS. 2 and 3 an arterial system according to a first embodiment of the invention, generally designated with reference numeral 100, comprises an arterial flow exchange system in the form of arterial device 200 (also referred to interchangeably herein as an aortic device) and a controller 300.

Arterial device 200 is in the form of an aortic cannula, in particular an aortic double-lumen cannula, comprising a distal portion 201 that is configured for being inserted into and accommodated within the aorta 1, in particular the ascending aorta 2, during operation of the system 100, and a proximal portion 202 that is configured for concurrently remaining outside of the aorta 1.

Device 200 comprises two internal lumens—a perfusion lumen 210 and an aspiration or suction lumen 220.

Distal portion 201 is in the form of a generally tubular elongate member 230, comprising a double lumen interior defining a respective distal perfusion lumen portion 210a of perfusion lumen 210, and a respective distal suction lumen portion 220a of suction lumen 220. Distal portion 201 further comprises a perfusion outlet port 240 and a suction inlet port 250.

Proximal portion 202 projects proximally from distal portion 201 and branches off from a generally tubular base member 232 having a double lumen interior contiguous with the double lumen interior of the distal portion 201, to two separate tubular members 234, 236 each continuing one or another of the lumens, thereby defining a respective proximal perfusion lumen portion 210b of perfusion lumen 210 and a respective proximal suction lumen portion 220b of suction lumen 220. The proximal portion 202 further comprises a perfusion inlet port 245 and a suction outlet port 255 at the proximal end 203 of the proximal portion 202, on the tubular members 234, 236 respectively.

The perfusion lumen 210 thus extends contiguously between the perfusion inlet port 245 and the perfusion outlet port 240, and provides fluid communication therebetween, via the proximal perfusion lumen portion 210b and the distal perfusion lumen portion 210a. Similarly, the suction lumen 220 thus extends contiguously from the suction outlet port 255 to the suction inlet port 250, and provides fluid communication therebetween, via the proximal suction lumen portion 220b and the distal suction lumen portion 220a.

The device 200 comprises an outer casing 237 and an internal partition wall 235 that separates the perfusion lumen 210 from the suction lumen 220 in the distal portion 201 and the base member 232.

Figure 4:
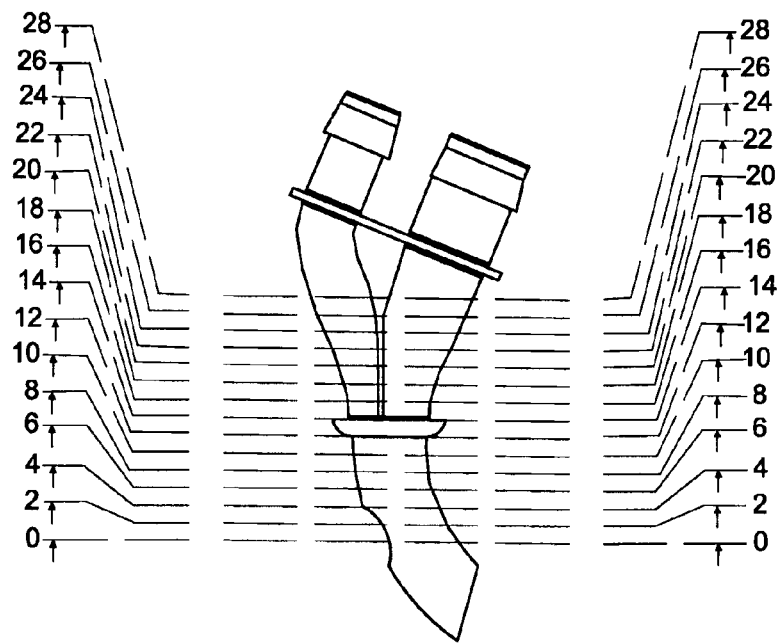
FIG. 4 is a side view of the aortic device of the embodiment of FIG. 3.
Figure 4A:
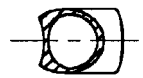
FIG. 4a to FIG. 4o are a series of cross-sectional views of the arterial device of the embodiment of FIG. 2, taken along sections 0 to 28, respectively, of FIG. 4.
Figure 4B:
FIG. 4p is a top view of the embodiment of FIG. 4.
FIG. 4q is a transverse cross-section of the embodiment of FIG. 4p taken along A-A.
Figure 4C:
Figure 4D:
Figure 4E:
Figure 4F:
Figure 4G:
Figure 4H:
Figure 4I:
Figure 4J:
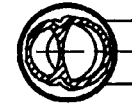
Figure 4K:
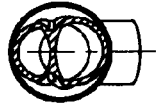
Figure 4L:
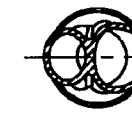
Figure 4M:
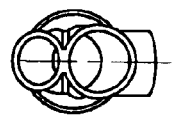
Figure 4N:
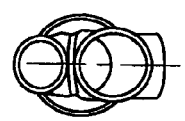
Figure 4O:
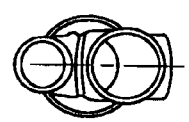
Figure 4P:
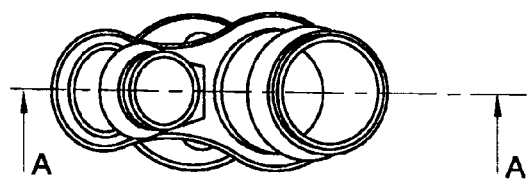
Figure 4Q:
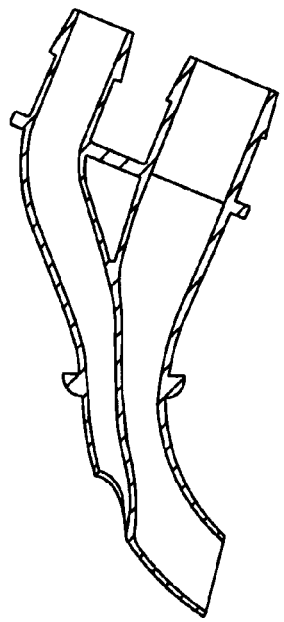

Referring also to FIGS. 4 to 4q, the perfusion lumen 210 is gently curved between the perfusion inlet port 245 and the perfusion outlet port 240, and has a transverse cross-section that smoothly changes between a generally circular form both at the perfusion inlet port 245 and at the perfusion outlet port 240, to a generally oblate form at an intermediate portion of the perfusion lumen 210 corresponding to the location of the partition wall 235. The curved path of the perfusion lumen 210 provides a net change in the direction of perfusion flow between the perfusion inlet port 245 and the perfusion outlet port 240 corresponding to angle a between the longitudinal axis A of the perfusion lumen 210 at the perfusion inlet port 245 and the longitudinal axis B of the perfusion lumen 210 at the perfusion outlet port 240. The gradual change in the flow direction of the perfusion flow in the perfusion lumen minimizes risk of haemolysis, for example, and enables relatively large perfusion flow rates to be provided to the aorta via the perfusion lumen 210.

In this embodiment, angle α is about 110 degrees, though in alternative variations of this embodiment angle α may be between about 90 degrees and about 180 degrees, for example.

Similarly, the suction lumen 220 is also gently curved between the suction outlet port 255 and the suction inlet port 250, and has a transverse cross-section than smoothly changes between a generally circular form at the suction outlet port 255 and a generally oblate form at the suction inlet port 240 and extending proximally along a portion of the suction lumen 220 corresponding to the location of the partition wall 235.

Thus, elongate member 230 is also mildly curved, and perfusion outlet port 240 is provided at the distal end 204 of the device 200, so that in use, the perfusion outlet port 240 faces the general downstream (antegrade) flow direction Q of the aorta. Distal edge 241 of the perfusion outlet port 240 is rounded (although in alternative variations of this embodiment this distal edge may be tapered or otherwise curved) to facilitate entry into the aorta 1. The perfusion outlet port 240 is also scarfed with respect to the perfusion lumen 210, and thus the plane of edge 241 is at an acute angle θ to a reference plane RP that is normal to the axis B. In this embodiment, angle θ is about 30 degrees, though in alternative variations of this embodiment angle θ may be between about 0 degrees and about 60 degrees, for example. The scarfing of perfusion outlet port 240 also facilitates entry of the distal portion 201 into the aorta 1.

The suction inlet port 250 is provided at the outer bend of the curved elongate member 230, generally opposed to the position of the perfusion outlet port 240 along axis B, so that in use of the device 200 the suction inlet port 250 faces the general upstream (retrograde) flow direction S of the aorta. The outer edge 251 of suction inlet port 250 is also scarfed in this embodiment and blends with the outer curved profile of the outside 338 of the distal portion 201, providing a relatively large inlet area as compared with the transverse cross-section of the suction lumen 220 in proximity to suction inlet port 250.

In operation of the device 200 and system 100, the suction inlet port 250 is upstream of the perfusion outlet port 240.

Device 200 is configured for operating within an artery, in particular the aorta 1, more in particular the ascending aorta 2, in a manner to provide fluid communication between the perfusion outlet port 240 and the suction inlet port 250 within the artery, aorta or ascending aorta, respectively, via the outside 338 of the distal portion 201 of the device 200.

Thus, distal portion 201 has an outside 338 (also referred to interchangeably herein as an outer surface of the distal portion 201) that in use of the device 200 does not occlude or otherwise obstruct the artery, aorta or ascending aorta in which the distal portion 201 is inserted, in particular within a region of the corresponding blood vessel between the location of the suction inlet port 250 and the location of the perfusion outlet port 240. Furthermore, the device 200, and in particular the distal portion 201, has an absence of any occlusion arrangement that is otherwise configured for occluding of obstructing the artery, in particular the aorta, more particularly the ascending aorta during use of the device such as to prevent such fluid communication between the perfusion outlet port 240 and the suction inlet port 250 via the outside 338.

Figure 8:
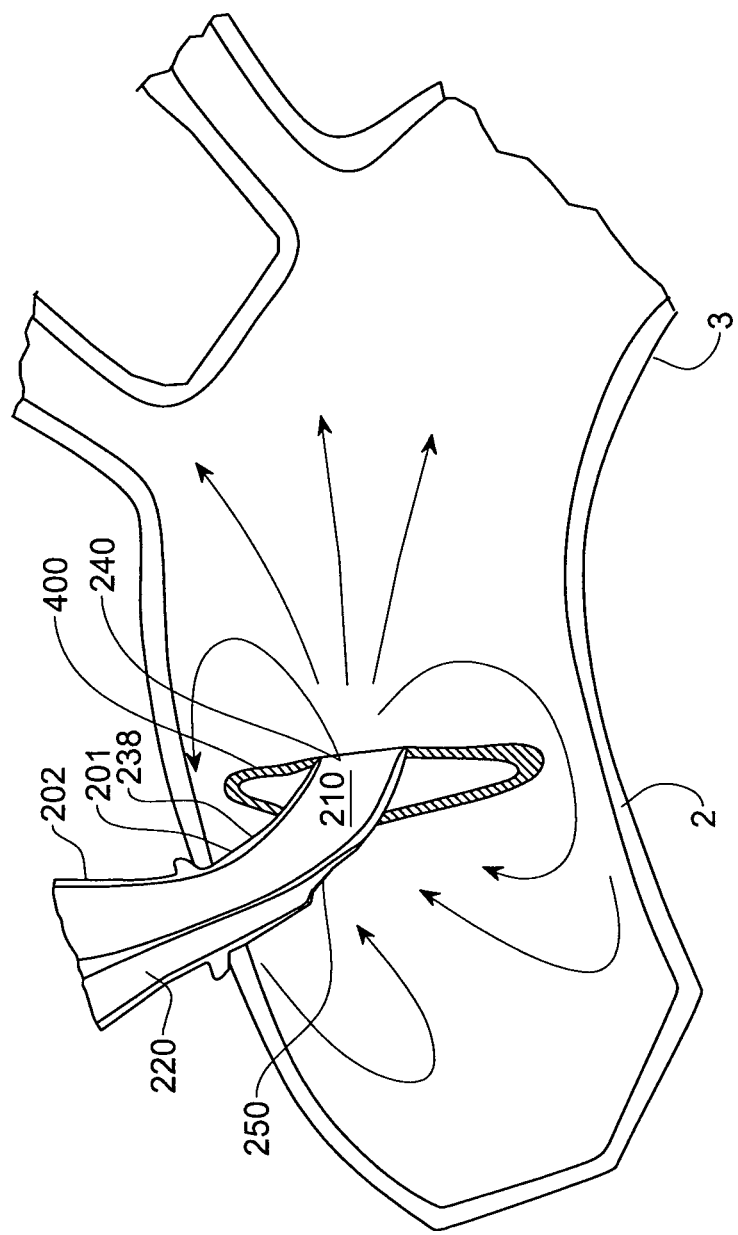
FIG. 8 is a cross-sectional side view of an alternative variation of the arterial device of the embodiment of FIG. 2, and schematically illustrates perfusion and suction flows within the aorta using the same.

In alternative variations of this embodiment in which the distal portion may be configured with one or more occlusion devices (for example inflatable balloons) positioned at a location inbetween the location of the suction inlet port and the location of the perfusion outlet port, and having an inoperative state in which the occlusion device does not occlude the blood vessel in which the device is installed, and an operative state in which the occlusion device occludes or blocks the blood vessel, such a device is operated with the occlusion device in the aforementioned inoperative state, or at least not in the aforementioned operative state—see for example the embodiment illustrated in FIG. 8.

In operation of the device 200 the suction inlet port 250 is in a position upstream of the perfusion outlet port 240, with respect to the antegrade flow direction Q.

At the distal end of the proximal portion 202 there is provided a collar 239. In use of the device 200, collar 239 abuts against an outer surface of the blood vessel in which the device is inserted, typically the aorta 1 and particularly the ascending aorta 2, and acts as a stop, preventing the device 200 from being inserted further. The location of the collar 239 with respect to the device 200 is also such as to ensure that when the device 200 is installed in the respective blood vessel, the outside 238 is suitably spaced from the internal walls of the blood vessel. In this embodiment the location of the collar 239 with respect to the device 200 is also such as to ensure that when the device 200 is installed in the respective blood vessel the perfusion outlet port 240 and/or the suction inlet port 250 is also centrally located within the blood vessel, i.e. centrally located with respect to the aortic lumen, so that the perfusion outlet port 240 and/or the suction inlet port 250, respectively, is generally uniformly spaced with respect to the internal walls of the blood vessel. In alternative variations of this embodiment, the collar 239 may be located with respect to the device 200 such as to ensure that when the device 200 is installed in the respective blood vessel the perfusion outlet port 240 is closer spaced with respect to one part than with respect to another part of the internal walls of the blood vessel.

The device 200 may be formed from substantially rigid and/or semi-rigid and medically compatible materials, including, for example medically suitable plastics, silicon, rubber or composite materials that are known in the art for use in aortic cannulation devices. The device 200 may thus be configured as disposable device, being made from disposable materials and disposed of after use with a patient. Alternatively, the device may be configured as an autoclavable or otherwise sterilizable and non-disposable device, and formed from stainless steel, titanium or other suitable metals or alloys or any other suitable materials.

Perfusion lumen 210 is configured for providing at least a nominal perfusion flow, i.e., having a nominal perfusion blood flow rate NFR, that is the minimum sufficient for providing adequate fluid flow to the body blood circulation system of the patient, i.e., a perfusion flow rate that is sufficient to sustain the minimum metabolic demands of the patient. In other words, the nominal perfusion flow comprises a fluid including oxygenated blood provided by the extra-corporeal blood oxygenation system (but may also comprise other fluids, for example saline solution), and corresponds to the blood flow that is the minimum normally provided to the aortic arch and the descending aorta of the patient by the heart of the patient at similar conditions. In practice, the nominal perfusion flow rate NFR is determined by the medical staff according to conventional practice, as discussed above in the "SUMMARY OF INVENTION" section above. Such nominal perfusion flow rate NFR is provided at a nominal flow velocity NFV that is below a threshold value V. The threshold value V is a flow velocity that above which is considered may cause haemolysis or other damage to the blood, for example due to the corresponding shear stresses induced in the blood.

In particular, the perfusion lumen 210 is configured for providing a target perfusion flow having a target perfusion flow rate TFR that is significantly greater than the aforesaid nominal perfusion flow rate NFR by a factor $\Delta FR$, referred to herein the excess perfusion flow rate (and also referred to herein interchangeably as the "excess flow rate"). In other words:

$$TFR=NFR+\Delta FR$$

The perfusion lumen 210 is configured for providing a maximum target perfusion flow having a corresponding maximum target perfusion flow rate $TFR_{max}$ that is greater than the aforesaid nominal perfusion flow rate NFR by a corresponding maximum excess perfusion flow rate $\Delta FR_{max}$, i.e., $$TFR_{max}=NFR+\Delta FR_{max}$$

Thus, in this embodiment, the perfusion lumen 210 comprises a minimum cross-sectional flow area that is correspondingly larger than would be otherwise be required for providing only the nominal perfusion flow rate NFR, in order to enable flow rates of up to the aforesaid maximum target perfusion flow rate $TFR_{max}$, but still at the flow velocities which are still below the aforesaid threshold value V.

In this embodiment, and by way of example, the perfusion lumen is configured for providing maximum target perfusion flow rate $TFR_{max}$ that is about 150% of the nominal perfusion flow rate NFR, and thus the corresponding maximum excess perfusion flow rate $\Delta FR_{max}$, is correspondingly about 50% of the nominal perfusion flow rate NFR.

In this embodiment, the perfusion lumen is configured for providing maximum target perfusion flow rate $TFR_{max}$ of greater than about 5.5 or 6 or 6.5 or 7 or 7.5 liters/minute, and a nominal perfusion flow rate NFR of about 4 to 5 liters/minute, depending on the particulars of the patient, for example, while the target perfusion flow rate TFR may vary in a range between about 3.3 l/min to about 4.5 l/min at nominal perfusion flow rate NFR of about 3 l/min, or wherein the target perfusion flow rate TFR may vary in a range between about 4.4 l/min to about 6 l/min at nominal perfusion flow rate NFR of about 4 l/min, increasing to a range between about 5.5 l/min to about 7.5 l/min at nominal perfusion flow rate NFR of about 5 l/min.

Thus, in this embodiment and at least some alternative variations of this embodiment of the invention, the target perfusion rate may thus vary between a minimum of about 110% of the nominal flow rate NFR, to a maximum of about 150%. In at least some other alternative variations of this embodiment or in other embodiments of the invention, the target perfusion rate may vary between a minimum of about 115% of the nominal flow rate NFR, to a maximum of about 150%. In at least some other alternative variations of this embodiment or in other embodiments of the invention, the target perfusion rate may vary between a minimum of about 115% of the nominal flow rate NFR, to a maximum of about 160%. In at least some other alternative variations of this embodiment or in other embodiments of the invention, the target perfusion rate may vary between a minimum of about 120% of the nominal flow rate NFR, to a maximum of about 150%. In at least some other alternative variations of this embodiment or in other embodiments of the invention, the target perfusion rate may vary between a minimum of about 125% of the nominal flow rate NFR, to a maximum of about 150%. In at least some other alternative variations of this embodiment or in other embodiments of the invention, the target perfusion rate may vary between a minimum of about 110% of the nominal flow rate NFR, to a maximum of about 175%. In at least some other alternative variations of this embodiment or in other embodiments of the invention, the target perfusion rate may vary between a minimum of about 115% of the nominal flow rate NFR, to a maximum of about 175%. In at least some other alternative variations of this embodiment or in other embodiments of the invention, the target perfusion rate may vary between a minimum of about 120% of the nominal flow rate NFR, to a maximum of about 175%. In at least some other alternative variations of this embodiment or in other embodiments of the invention, the target perfusion rate may vary between a minimum of about 125% of the nominal flow rate NFR, to a maximum of about 175%. In at least some other alternative variations of this embodiment or in other embodiments of the invention, the target perfusion rate may vary between a minimum of about 120% of the nominal flow rate NFR, to a maximum of about 170%.

In this embodiment, and by way of example, the perfusion lumen 210 has an internal diameter of about 7.7 cm at the perfusion inlet port 245 and an internal diameter of about 7.6 cm at the perfusion outlet port 240. The suction lumen 220 has an internal diameter of about 4.4 cm at the suction outlet port 255, and the suction inlet port 250 has a maximum width of about 8.8 cm due to the scarfing thereof. Furthermore, by way of further example, FIG. 4a to FIG. 4o show geometrically consistent and accurate cross-sections of the embodiment of FIG. 4, taken along numerically labeled sections "0" to "28", respectively, of FIG. 4. It is to be further noted that the numerical label for each of these sections refers to a spacing in mm of the respective section from the first section illustrated in FIG. 4a. Thus, for example, FIG. 4j refers to the cross-section at section "18", which is at 18 mm from the section depicted in FIG. 4a. As a datum, section 12 illustrated in FIG. 4g is at the proximal end of the distal portion of the device.

The nominal perfusion blood flow rate NFR may of course vary from patient to patient, and is generally a function of, inter alia, body weight, age, sex and general health of the particular patient, and may also vary with time, activity and so on. However, according to at least this embodiment of the invention, the target perfusion flow rate TFR and the maximum target perfusion flow rate $TFR_{max}$ are related to the specific nominal perfusion blood flow rate NFR that is unique to the particular patient that is being treated with the system 100 and device 200, as determined by the medical staff treating the patient.

The suction lumen 220 has a minimum cross-sectional flow area that is smaller than the minimum cross-sectional flow area of the perfusion lumen 210, and in this embodiment is configured for providing a suction flow rate SFR that can be varied from zero to a maximum suction flow rate $SFR_{max}$ that is generally similar to the corresponding maximum excess perfusion flow rate $\Delta FR_{max}$.

The perfusion inlet port 245 is configured for being connected to, and thus for receiving oxygenated blood from, a suitable perfusion source 320, for example a heart lung machine (also referred to interchangeably herein as a bypass-oxygenator machine) or any other extra-corporeal blood oxygenation system, which are well known in the art, and of which there exist many commercially available examples.

A suitable pump 325, for example a peristaltic pump, pumps oxygenated blood from the perfusion source 320 to the device 200. Pump 325 is configured for providing a controllable perfusion flow rate at least up to the maximum target perfusion flow rate $TFR_{max}$ for the particular patient being treated by system 100, and is variably controllable (by controller 300) to provide perfusion flow rates from nominally zero to at least up to the maximum target perfusion flow rate $TFR_{max}$.

The pump 325 is operatively connected to, and is controlled by, controller 300. Thus, controller 300 is configured for controlling the pump 325 to provide any desired perfusion flow rate in the range between zero and at least the maximum target perfusion flow rate $TFR_{max}$.

The suction outlet port 255 is configured for being connected to, and thus for returning blood to, a suitable suction source 345, for example in the form of a medical suction pump, for example a peristaltic pump. Suitable medical suction pumps capable of aspirating or sucking blood are well known in the art, and of which there exists many commercially available examples. In alternative variations of this embodiment, the suction source 345 may comprise a fluid suction line, suitable for suctioning blood or other liquids. In any case, the suction source 345 is selectively controllable, and is operatively connected to, and is controlled by, controller 300.

The suction source 345 is configured for providing a variably controllable suction flow rate from nominally zero to at least the maximum suction flow rate $SFR_{max}$. The controller 300 is configured for selectively controlling the suction source 345 to provide any desired suction flow rate in the range between zero and at least the maximum suction flow rate $SFR_{max}$.

In at least some operational modes of the system 100, the suction source 345 sucks or aspirates blood via the device 200 and into a suitable receiving volume 340. In some alternative variations of this embodiment, the blood collected at receiving volume 340 may be subsequently suitably processed to remove embolic debris and may be then supplied to the perfusion source 320 to provide a closed system.

Thus, in this embodiment and at least some alternative variations of this embodiment of the invention, the suction flow rate may thus vary between a minimum of about 10% of the nominal flow rate NFR, to a maximum of about 50%. In at least some other alternative variations of this embodiment or in other embodiments of the invention, the suction flow rate may vary between a minimum of about 15% of the nominal flow rate NFR, to a maximum of about 50%. In at least some other alternative variations of this embodiment or in other embodiments of the invention, the suction flow rate may vary between a minimum of about 15% of the nominal flow rate NFR, to a maximum of about 60%. In at least some other alternative variations of this embodiment or in other embodiments of the invention, the suction flow rate may vary between a minimum of about 20% of the nominal flow rate NFR, to a maximum of about 50%. In at least some other alternative variations of this embodiment or in other embodiments of the invention, the suction flow rate may vary between a minimum of about 25% of the nominal flow rate NFR, to a maximum of about 50%. In at least some other alternative variations of this embodiment or in other embodiments of the invention, the suction flow rate may vary between a minimum of about 10% of the nominal flow rate NFR, to a maximum of about 75%. In at least some other alternative variations of this embodiment or in other embodiments of the invention, the suction flow rate may vary between a minimum of about 15% of the nominal flow rate NFR, to a maximum of about 75%. In at least some other alternative variations of this embodiment or in other embodiments of the invention, the suction flow rate may vary between a minimum of about 20% of the nominal flow rate NFR, to a maximum of about 75%. In at least some other alternative variations of this embodiment or in other embodiments of the invention, the suction flow rate may vary between a minimum of about 25% of the nominal flow rate NFR, to a maximum of about 75%. In at least some other alternative variations of this embodiment or in other embodiments of the invention, the suction flow rate may vary between a minimum of about 20% of the nominal flow rate NFR, to a maximum of about 70%.

Thus, in operation the system 100 comprises arterial device 200 and extra-corporeal circulation system 290, which comprises controller 300, pump 325, perfusion source 320 and suction source 345, and optionally also receiving volume 340.

In this embodiment, controller 300 comprises a suitable computer system or the like, which may be preprogrammed to operate the system 100 automatically in one or more operating modes, and/or which may be programmed for operating in one or more operating modes manually or interactively, according to operator input. In alternative variations of this embodiment, the controller 300 may instead comprise any other suitable control system, for example an electronic control system, a mechanical control system, or a hydraulic control system, each respectively configured to selectively provide one or more desired operating modes for the system 100.

The system 100 is particularly configured for causing embolic debris that may be present at least in the ascending aorta 2 to be diverted or directed to the suction inlet port 250 and out of the aorta 1 via the suction lumen 220, in particular at least a majority, and preferably all, the embolic debris, and thus prevent or minimize migration of embolic debris from the ascending aorta 2 to the aortic arch 3. At the same time, the system 100 is also configured for providing the patient with the nominal perfusion flow required for the patient when the heart is not functioning, and/or, for providing the patient with a supplemental perfusion flow required for the patient when the heart is beginning to function again after cardiac surgery and is not yet itself providing the patient with the full required nominal perfusion flow.

As will become apparent, operation of the system 100 to remove the aforesaid embolic debris does not of itself cause or potentially cause more embolic debris to be created. Furthermore the system 100 can be operated to allow such embolic debris removal operation to be carried out while providing a nominal perfusion flow to the body circulation system, and for the embolic debris removal operation to be phased out, while still providing the required nominal perfusion flow to the patient's body circulation system. Alternatively, the system 100 can be operated to continue removing embolic debris, while phasing out the nominal perfusion flow function, as the heart begins to take over perfusion of the body from the extracorporeal circulation system.

The system 100 can thus operate in a number of different operating modes and can switch between different operating modes smoothly. Prior to operating the system 100, the device 200 must be properly positioned in the aorta, the distal portion 201 having been introduced and installed in the ascending aorta 2 of the patient for antegrade deployment by any suitable procedure, for example including any suitable procedure for installing a conventional aortic cannulation device. Such a procedure may include, for example, providing a purse string suture in the wall of the ascending aorta, and an aortotomy incision is made inside the purse string. The distal portion 201 is introduced into the aorta via this incision, and the device 200 secured in place, for example by suturing the collar 239 to the wall of the aorta.

Thereafter, the heart 9 may be isolated from the aorta for conducting the required cardiac procedure or surgery, for example CPB, by closing off the upstream end of the ascending aorta 2, for example using clamps on the outside of the ascending aorta 2, or by using an occlusion device within the ascending aorta, upstream of the distal portion 201, and by providing oxygenated blood to the body circulation system from perfusion source 320 via the device 200. The heart may be stopped using any one of a variety of techniques which are well known in the art, as required for the cardiac surgery.

Nominal Perfusion Operating Mode

In the nominal perfusion operating mode (NPOM), the system 100 operates to provide oxygenated blood at least at the nominal perfusion flow rate NFR to the body circulation system. In NPOM mode, the controller 300 is configured for controlling the pump 325 to deliver oxygenated blood from perfusion source 320 to the device 200 via the perfusion lumen 210 at the nominal perfusion flow rate NFR, while the suction source 345 is substantially inoperational or on standby, and no significant suction is induced via the suction lumen 220.

In NPOM mode, the perfusion flow rate may be selectively increased or decreased according to the metabolic needs of the patient, for example, and the device 200 operates in a manner substantially similar to conventional aortic perfusion cannulation devices.

In NPOM mode, the perfusion flow rate may also be incrementally reduced to zero when the heart is again beating and is in fluid communication with the aorta, and the heart takes over perfusion of the body circulation. However the NPOM mode is in general only used in this manner when there is no suspicion or risk of embolic debris that may be present and potentially harmful to the patient. Where such a suspicion or risk exists, the embolic debris removal operating mode may be used, as described in greater detail below.

Embolic Debris Removal Operating Mode

In the embolic debris removal operating mode (EROM), the system 100 operates to provide oxygenated blood at least at the nominal perfusion flow rate NFR to the body circulation system, while concurrently removing embolic debris and preventing the same from flowing to the aortic arch and possibly therefrom to the cerebral circulation system.

In EROM mode, the controller 300 is configured for controlling the pump 325 to deliver oxygenated blood from perfusion source 320 to the device 200 via the perfusion lumen 210 at a desired target perfusion flow rate TFR, while controlling the suction source 345 to provide a suction flow rate SFR via the suction lumen 220.

In standard EROM mode, the desired target perfusion flow rate TFR and the suction flow rate SFR are controlled in a manner to match the suction flow rate SFR to the excess perfusion flow rate ΔFR that corresponds to the target perfusion flow rate TFR, this matching being according to a desired matching level. The desired matching level may range from a minimum matching level, in which the suction flow rate SFR is a percentage of the excess perfusion flow rate ΔFR that is less than 100%, such as about 25%, though preferably not less than about 50%, to a maximum matching level, in which the suction flow rate SFR is fully (100%) matched to and is substantially equal to the excess perfusion flow rate ΔFR. In some circumstances, the matching level may be even less than 25%, for example when the patient is experiencing bleeding.

In other circumstances, the matching level may be greater than 100%, for example when there is a large amount of embolic debris, and the nominal flow rate NFR to the patient is temporarily reduced pro-rate, to avoid having to increase the target perfusion rate further.

In regular operation of the system 100 in EROM mode, the matching level is maintained at about 100%, and the matching level is deviated away from this 100% matching level when there is a special need to do so.

Figure 5:
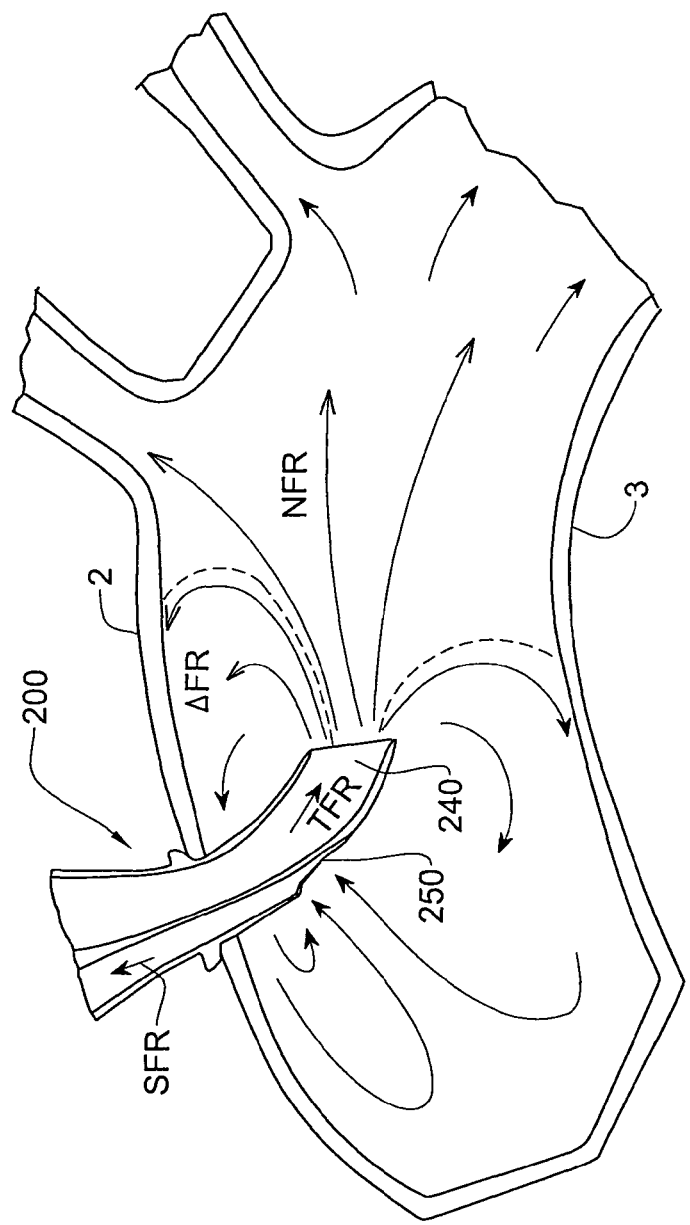
FIG. 5 illustrates schematically perfusion and suction flows within the aorta using the embodiment of FIG. 1.

Without being bound by theory, and referring to FIG. 5, the inventors suggest that by providing a target perfusion flow rate TFR that includes the nominal perfusion flow rate NFR and the corresponding excess perfusion flow rate ΔFR, and by concurrently providing a suitable suction flow rate SFR, a recirculation flow field is set up in the ascending aorta between the perfusion outlet port 240 and the suction inlet port 250, which are in fluid communication one with the other in use of the system. In steady state conditions, an amount of the blood in the aorta is being continually sucked into the suction lumen 220 via the suction port 250 at the suction flow rate SFR, and concurrently the same amount of blood is being replaced by the perfusion flow provided by the perfusion outlet port 240 at a flow rate corresponding to the suction flow rate SFR, for conservation of mass flow. Thus, at steady state, at least a proportion P of the target perfusion flow rate TFR is effectively being recirculated into the ascending aorta in retrograde flow, and eventually sucked into the suction inlet port 250. According to at least this embodiment of the invention, this proportion P is fully provided by all the excess perfusion flow rate ΔFR of the target perfusion flow rate TFR, so that the remainder of the perfusion flow, i.e., the nominal perfusion flow rate NFR, concurrently continues into the aortic arch 3 to supply the minimum metabolic needs of the body via the body circulation system. Thus, the matching level between the suction flow rate SFR, and the excess perfusion flow rate ΔFR is 100%. In alternative variations of this embodiment, this proportion P is fully provided by a first part of the excess perfusion flow rate ΔFR of the target perfusion flow rate TFR, so that the remainder of the perfusion flow, i.e., the nominal perfusion flow rate NFR, plus the remainder of the excess perfusion flow rate ΔFR concurrently continues into the aortic arch 3 to supply more than the minimum metabolic needs of the body via the body circulation system, and thus the matching level between the suction flow rate SFR, and the excess perfusion flow rate ΔFR is substantially less than 100%.

Figure 6:
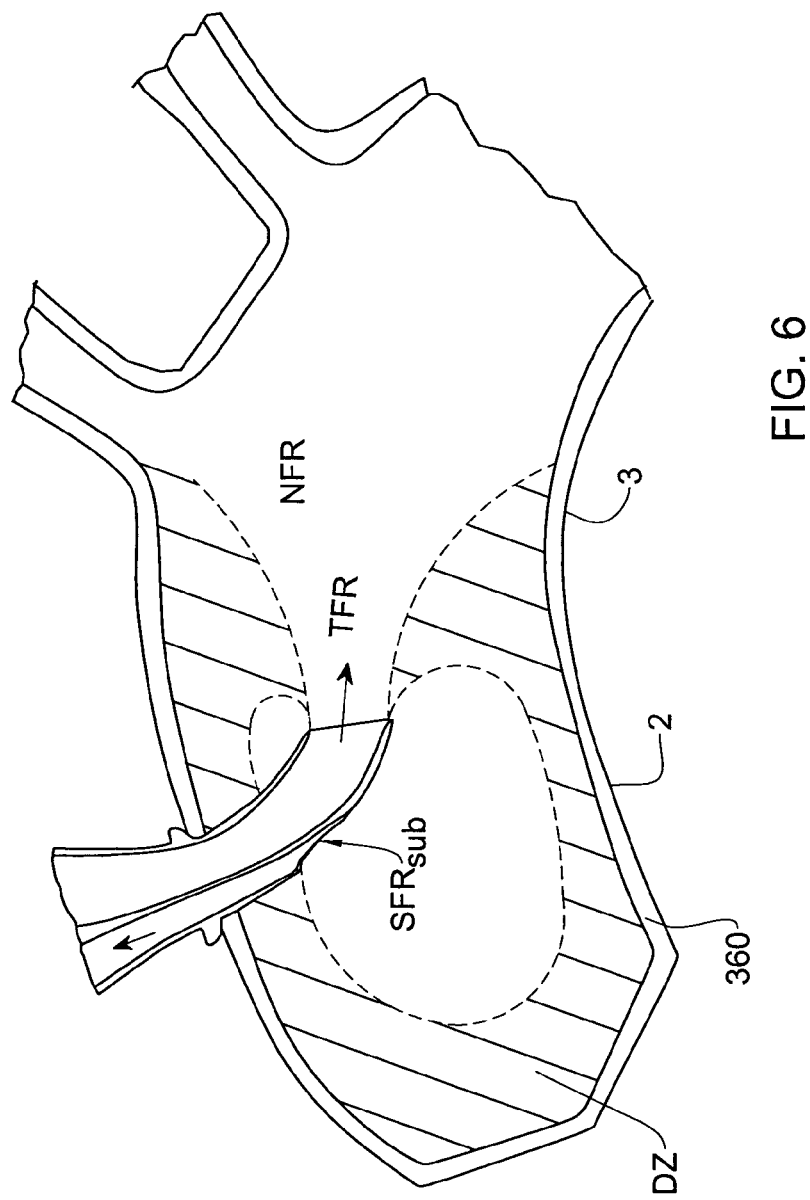
FIG. 6 illustrates schematically perfusion and suction flows within the aorta using the embodiment of FIG. 1, where the suction flow rate is below a threshold value.

Referring to FIG. 6, and again without being limited to theory, the inventors suggest that at relatively low levels of suction flow rate SFR, designated herein as $SFR_{sub}$, the recirculation flow field, indicated in the figure by broken line 360, is relatively small and may not extend to the internal walls 10 of the ascending aorta 2, leaving a stagnation zone or "dead zone" DZ in the ascending aorta 2 that is substantially unaffected by this recirculation flow field. Under these conditions embolic debris that may exists within the dead zone DZ is also substantially unaffected by the recirculation field and is effectively free to migrate to the aortic arch 3, with potentially serious consequences to the patient. Under these conditions, even if the target perfusion flow rate TFR is further increased but while maintaining the low suction flow rate $SFR_{sub}$, the dead zone still remains, and only the perfusion rate into the body circulation system is increased to above the nominal perfusion flow rate NFR.

Figure 7:
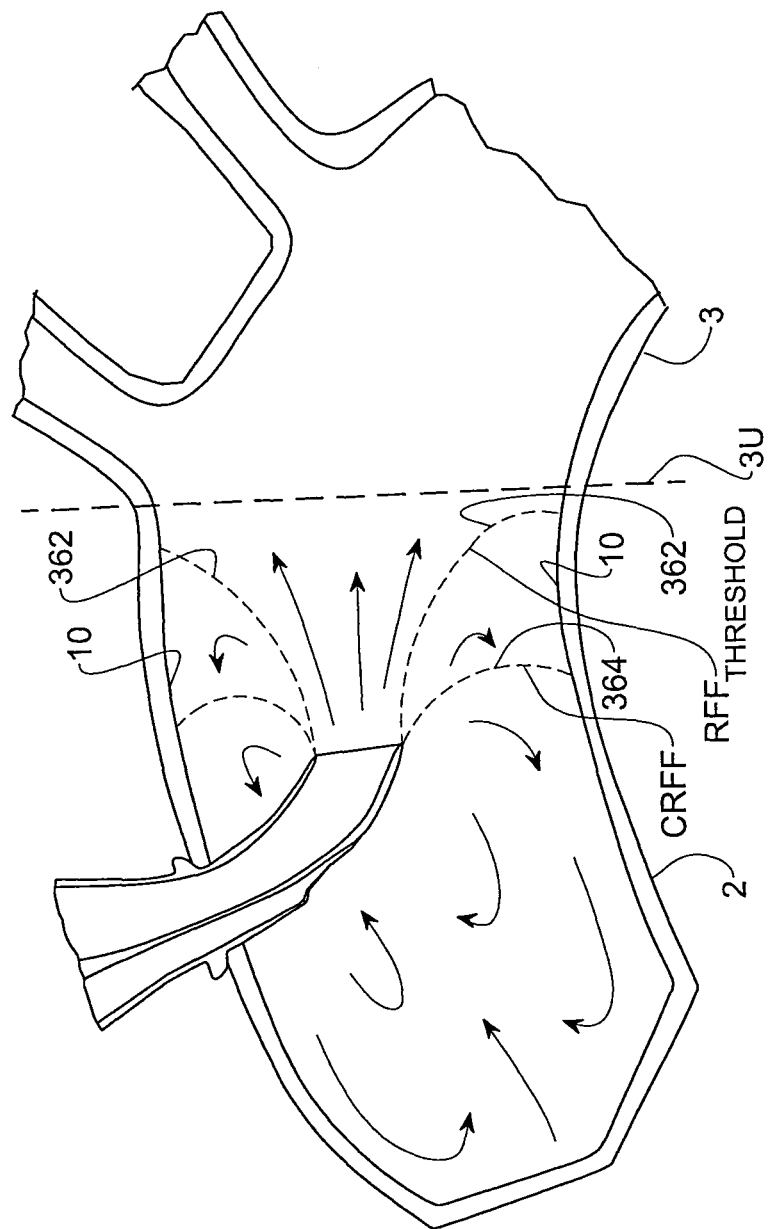
FIG. 7 illustrates schematically perfusion and suction flows within the aorta using the embodiment of FIG. 1, where the suction flow rate is at or above a threshold value.

Referring to FIG. 7, and again without being limited to theory, the inventors further suggest that as the suction flow rate SFR is increased from the low suction flow rate $SFR_{sub}$ to a threshold value of suction flow rate SFR, designated herein as $SFR_{threshold}$, (and concurrently the target perfusion rate TPR is also increased to a corresponding threshold target perfusion rate $TPR_{threshold}$ so that at least a minimum perfusion flow is still being provided to the body circulation system at the nominal perfusion flow rate NFR), the recirculation flow field gets larger to a threshold recirculation flow field $RFF_{threshold}$. At this threshold suction flow rate $SFR_{threshold}$, the threshold recirculation flow field $RFF_{threshold}$ is such that the retrograde flow originating from the corresponding proportion P of the increased target perfusion rate TPR and that is being effectively sucked in via the suction inlet port 250 effectively reduces the dead zone DZ to zero, so that the threshold recirculation flow field $RFF_{threshold}$ now occupies the upstream portion of the ascending aorta, or at least so that the threshold recirculation flow field $RFF_{threshold}$ extends to the walls 10 of the ascending aorta 2 (the downstream limit of the threshold recirculation flow field $RFF_{threshold}$ being indicated by the broken line at 362) such as to effectively prevent migration of embolic debris into the aortic arch 3 from the ascending aorta 2, or to reduce potential migration of embolic debris. Thus, under these conditions any embolic debris in the ascending aorta 2 is eventually diverted to the suction inlet port 220 and removed via the suction cannula 220.

Referring still to FIG. 7, and again without being limited to theory, the inventors further suggest that as the suction flow rate SFR is increased further above the threshold value of suction flow rate $SFR_{threshold}$, (and concurrently the target perfusion rate TPR is also increased from the corresponding threshold target perfusion rate $TPR_{threshold}$ so that at least a minimum perfusion flow is still being provided to the body circulation system at the nominal perfusion flow rate NFR), the recirculation flow field RFF gets larger and/or stronger, and is referred to herein as the corresponding closed recirculation flow field CRFF. Under such conditions, there is even less risk of migration of embolic debris into the aortic arch 3 than at the aforesaid threshold suction flow rate $SFR_{threshold}$, the downstream limit 364 of corresponding closed recirculation flow field CRFF moves further upstream within the ascending aorta 2.

Thus, the threshold suction flow rate $SFR_{threshold}$ may be defined as the minimum suction flow rate in which there is significant reduction in migration of embolic debris into the aortic arch 3 from the ascending aorta 2, and preferably that such migration of embolic debris is effectively prevented. While the precise value of the threshold suction flow rate $SFR_{threshold}$ may vary according to the particular circumstances of the patient, inventors consider that the threshold suction flow rate $SFR_{threshold}$ may vary between about 10% and about 25% of the nominal perfusion flow rate NFR for a particular patient. Thus, example of values for the threshold suction flow rate $SFR_{threshold}$ may be 10% or 15% or 20% or 25% of the nominal perfusion flow rate NFR for a particular patient.

Thus, in such conditions, in which the suction flow rate SFR is at or above the threshold value of suction flow rate $SFR_{threshold}$, (and concurrently the target perfusion rate TPR is also at or above the corresponding threshold target perfusion rate $TPR_{threshold}$ so that perfusion flow is still being provided to the body circulation system at least at the nominal perfusion flow rate NFR), there is a qualitative as well as a quantitative change in the characteristics and/or effect of the flows provided within the aorta, in particular the ascending aorta, leading to substantial reduction or elimination of migration of embolic debris into the aortic arch 3, as compared with the flow provided within the aorta at much lower flow rates.

In any case, a working value for the threshold suction flow rate $SFR_{threshold}$ may be ascertained or estimated in a number of ways, which may be patient-unique or general. For example, the anatomy and flow parameters of the aorta of the particular patient or of a standard adult aorta (defined in a suitable manner, for example having an anatomy that is averaged across the population or a statistically significant sample thereof) may be physically modeled, so that a physical model of the aorta is constructed and tested with suitable particles that model the embolic debris. Fluid flows into and out of the device 200 (properly installed in the model to simulate the installation in a real aorta) are provided with fluid that models blood, and the flows are controllably and selectively varied, and the effect on particle migration to the aortic arch, the particles originating upstream of the aorta and/or from the perfusion lumen of the device 200 is determined. At the same time the perfusion flow velocity is preferably kept to below the threshold value V. Thereby, the threshold suction flow rate $SFR_{threshold}$ may be empirically determined.

Alternatively, a computer model simulation of the patient's aorta may be created, and a suitable computerized flow analysis conducted in the computer environment of the fluid flows into and out of the aortic device (that is also modeled in the computer simulation), in a computer model similar to the physical model, mutatis mutandis.

In any case, in at least one embodiment of the standard EROM mode, the suction flow rate SFR is set well above the threshold suction flow rate $SFR_{threshold}$, at or close to the maximum suction flow rate $SFR_{max}$, and concurrently perfusion is provided at the maximum target perfusion rate $TFR_{max}$, so that the full corresponding maximum excess perfusion flow rate $\Delta FR_{max}$ is effectively used for the removal or potential removal of embolic emboli from the ascending aorta, while sufficient perfusion is provided at the aforesaid nominal perfusion flow rate NFR for the needs of the patient, and while maintaining the target perfusion flow rate flowing at flow velocities below the threshold velocity V.

The EROM mode can be used whenever necessary or desired, for example in the following situations:
(a) Prior to clamping or occluding the aorta, in anticipation of and to collect possible embolic debris that may be formed thereafter.
(b) After clamping or occluding the aorta, to collect possible embolic debris that may be formed as a result thereof
(c) After unclamping or removing the occlusion in the aorta, to collect possible embolic debris that may be formed as a result thereof
(d) Whenever there is a suspicion that embolic debris may be found in the ascending aorta, or where such embolic debris is detected.
(e) Throughout the cardiac procedure, whenever there is a need to provide artificial perfusion to the body circulation system.

Between (b) and (c), i.e., after it is considered that any possible embolic debris has been diverted and removed via the system 100, but before it is desired to unclamp or remove the occlusion in the aorta, it is possible to change operating mode from EROM mode to NPOM mode to continue providing nominal perfusion to the body circulating system. This switchover in operating modes only requires the suction flow rate SFR to be gradually decreased to zero, while concurrently decreasing the target perfusion rate TFR to the nominal perfusion flow rate NFR.

Conversely, just before it is desired to unclamp or remove the occlusion in the aorta, it is possible to change operating mode back to EROM mode from NPOM mode to begin again suctioning, with a suction flow rate increasing from zero to the required value, and the target perfusion flow rate TFR similarly increasing, to provide sufficient flow for the recirculation field and to concurrently continue providing nominal perfusion to the body circulating system.

If after (c) there is still suspicion or evidence of embolic debris in the ascending aorta, the EROM mode can be continued further until all the embolic debris is removed, prior to starting the heart again, after which if there is no further embolic debris the system 100 can switch to operating in NPOM mode, and then reduce the actual perfusion rate to zero as the heart takes over the function of providing oxygenated blood to the body.

Alternatively, it is possible to continue operating in EROM mode even once the heart starts again, to eliminate embolic debris that originates upstream of the aorta. In particular, the system may be operated in such circumstances in de-airing mode (DAM), to remove embolic debris in the form of air bubbles. In fact, in such a DAM mode, and when the heart is operating and providing part or all of the nominal perfusion, the system may be configured for providing a suction flow rate that is higher than required in other operating modes.

Referring to (e) above, it may be desired to use EROM mode throughout the cardiac procedure, whenever there is a need to provide artificial perfusion to the body circulation system, for example when there is a risk of embolic debris being generated by the extra-corporeal circulation system and introduced into the patient via the perfusion lumen. Thus EROM may completely replace NPOM mode, and is used continuously until the end of the procedure.

Thus, it is evident that the system 100 may be used in EROM mode continuously, for example from just before it is desired to clamp or provide the occlusion in the aorta, or even as soon as the device 200 is installed, to after the aorta is unclamped or the occlusion removed therefrom. In such continuous EROM mode, the suction flow rate and the target flow rate may be set at a desired preset level, or may be varied, but always maintaining a suitable suction flow and a suitable excess perfusion flow.

It is also evident that the system 100 may be used in an intermittent manner, in which high target perfusion flow rates TFR and high suction flow rates SFR are provided when there is danger or risk of embolic debris, for example during clamping and unclamping of the aorta, and reducing these flow rates to provide zero suction flow rate or low flow rates at other times.

In at least some alternative variations of this embodiment a suitable sensor system may be provided to detect the presence of embolic debris in the ascending aorta, for example, and for automatically switching the system to EROM mode (or possibly automatically increasing further the target perfusion flow rates TFR and the suction flow rate SFR, if already in EROM mode) when embolic debris is detected. Such a sensor may be based on Transcranial Doppler technology (referred to in the art as TCD), for example.

Once the heart has fully taken over providing perfusion for the body, the device 200 may be removed, for example in a manner used conventionally for removing conventional aortic cannulation devices.

It is to be noted that in the absence of contact between the distal portion 201 and the walls 10 of the aorta (other than due to penetration of the distal portion 201 into the aorta), operation of the system 100 or stopping operation of the system 100 at least according to this embodiment does not per se result in the significant or actual creation of new embolic debris.

Figure 3A:
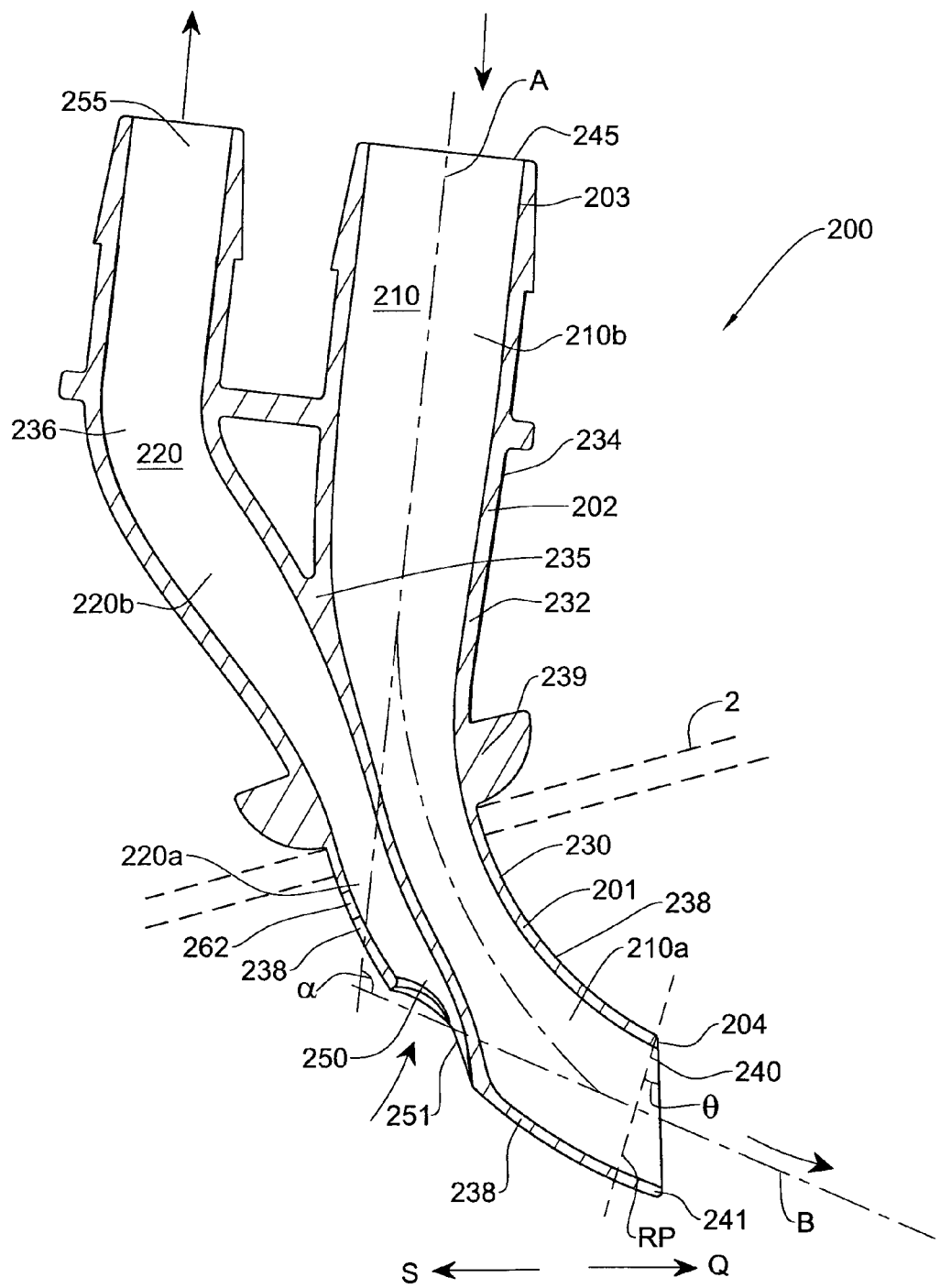
FIG. 3a is a cross-sectional side view of an alternative variation of the embodiment of FIG. 3.

An alternative variation of the first embodiment is illustrated in FIG. 3(a), in which the device 200 is further modified to include an additional suction inlet port in the form of an air bubble suction inlet 262 that is particularly configured for removing embolic emboli in the form of air bubbles that may be released into the aorta when the aorta is unclamped, for example, and thus the arterial device 200 of FIG. 3(a) may be operated as a de-airing device. As may be seen, the air bubble suction inlet 262 is in communication with the suction lumen 220, and is located in the distal portion 201 at a location that, in operation of the device 200, is close to the inner wall of the aorta 2, preferably at a gravitationally high point in the aortic walls, facilitating migration of air bubbles thereto for subsequent removal thereof.

An alternative variation of the first embodiment is illustrated in FIG. 8, in which the device 200 is further modified to include a selectively enlargable device 400 on the external wall 238 of the distal portion 201. The enlargeable device 400 in this embodiment comprises an inflatable annular balloon member 410 than may be selectively inflated from a deflated condition, in which the balloon member 410 is close to the external wall 238, to an inflated condition, illustrated in FIG. 8, in which the balloon member 410 partially obstructs the cross-section of the ascending aorta, but still allows for significant fluid communication between the inlet suction port 250 and the perfusion outlet port 250. In particular, the balloon member 410 does not abut or engage with the aortic walls 10, and preferably does not come in contact the aortic walls 10, in use of the device and when the balloon member 410 is in the inflated condition. Use of this embodiment in NPOM mode is similar to that described herein for the first embodiment, mutatis mutandis, and in this mode the balloon member may be inflated or deflated. Similarly, use of this embodiment in EROM mode is similar to that described herein for the first embodiment, mutatis mutandis, and in this mode the balloon member may also be inflated or deflated, though when inflated, it may operate more efficiently in removing embolic debris even where the suction flow rate is lower than the aforesaid threshold suction flow rate $SFR_{threshold}$.

Figure 9:
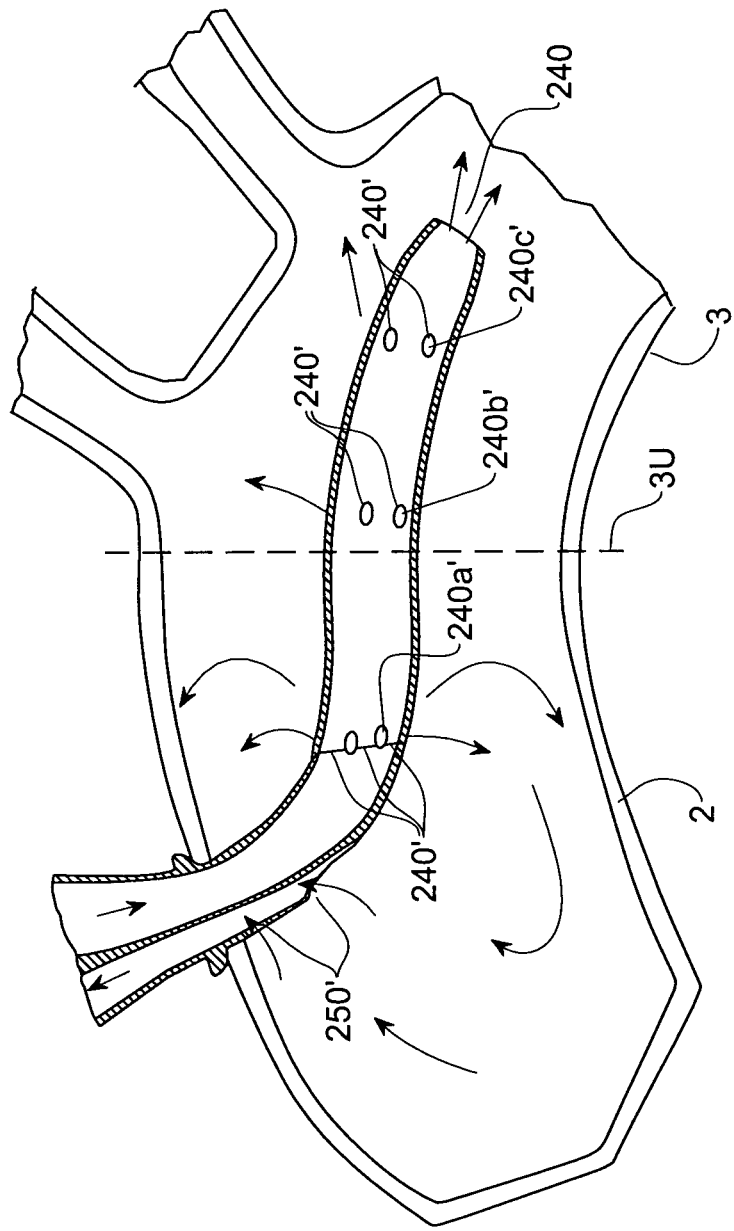
FIG. 9 is a cross-sectional side view of another alternative variation of the arterial device of the embodiment of FIG. 2, and schematically illustrates perfusion and suction flows within the aorta using the same.

Another alternative variation of the first embodiment is illustrated in FIG. 9, in which the distal portion, designated 201', is similar to the distal portion 201 disclosed for the first embodiment, mutatis mutandis, with some differences. These differences include:

in distal portion 201' of the embodiment of FIG. 9, the distal end 204' of the device now extends into the aortic arch 3;

distal portion 201' includes a plurality of perfusion outlet ports 240' rather than the single perfusion outlet port 240 of the first embodiment;

distal portion 201' includes a plurality of suction inlet ports 250' rather than the single suction inlet port 250 of the first embodiment illustrated in FIG. 3, and thus may also include a de-airing suction port similar to that illustrated for embodiment of FIG. 3a.

Further, at least one or more perfusion outlet ports 240', designated 240a' are located at a position to be within the ascending aorta 2 when the aortic device is installed therein, similar to the position of the single perfusion outlet port 240 of the first embodiment, and have a combined exit flow area of $A_a$. Another group of one or more perfusion outlet ports 240', designated 240b' are located at a position to be within the aortic arch 3, close to the upstream end 3U thereof, when the arterial device is installed therein, and have a combined exit flow area of $A_b$. Another group of one or more perfusion outlet ports 240', designated 240c' are located at a position to be within the aortic arch, further downstream of perfusion outlet ports 240b', and have a combined exit flow area of $A_c$. Finally, the distal end 204' comprises another outlet port 240', designated 240d', and having an exit flow area of $A_d$. (Optionally, further perfusion outlet ports may be provided at different locations on the distal end 201'.)

The combined exit flow areas of all the perfusion outlet ports 240' is such as to provide the desired target perfusion flow rate PFR, while maintaining the exit velocity below the threshold velocity V. Furthermore, the relative sizes exit flow area of $A_a$, $A_b$, $A_c$ and $A_d$ can be set so that the desired flow at the nominal perfusion flow rate NPR is provided via perfusion outlet ports 240c' and perfusion outlet ports 240d', for example, while the excess perfusion flow at excess perfusion flow rate ΔFR, or at least the proportion P of the target perfusion flow rate TFR for matching the suction flow rate SFR, is provided via perfusion outlet ports 240a' and perfusion outlet ports 240b'. Alternatively, the perfusion flow from the perfusion outlet ports 240b' may be used for the nominal perfusion flow rate NPR instead of for the excess perfusion flow rate ΔFR.

Operation of the embodiment of FIG. 9 is similar to that disclosed herein for the first embodiment, mutatis mutandis.

In yet other alternative variations of the first embodiment or of the above variations thereof, the arterial device may comprise a perfusion lumen arrangement having a plurality of perfusion lumens, each in fluid communication with one or more suitable perfusion sources, and each one providing perfusion flow via the same perfusion outlet port or via a plurality of perfusion outlet ports, and/or, the arterial device may comprise a suction lumen arrangement having a plurality of suction lumens, each in fluid communication with one or more suitable suction sources, and each one providing suction flow via the same suction inlet port or via a plurality of suction inlet ports.

A feature of the first embodiment and at least some alternative variations thereof is that a single entry point is required in the aorta, in particular the ascending aorta, for providing the dual functions of providing perfusion to the body circulation system and for removing embolic debris (and optionally also de-airing), and furthermore, the same arterial device may be used for providing perfusion where it is not desired to operate the embolic debris removal functionality of the arterial device.

The first embodiment, or at least some alternative variations thereof, may be operated according to one or more of the following operating parameters:

wherein said nominal perfusion flow rate is in the range between about 3 liters per minute to about 5 liters per minute;

wherein said target flow rate is in the range between about 3.3 liters per minute to about 7.5 liters per minute;

wherein said excess perfusion flow rate is in the range between about 0.3 liters per minute to about 2.5 liters per minute;

wherein said suction flow rate is greater than 0.5 liters per minute;

wherein said suction flow rate is greater than 0.75 liters per minute;

wherein said suction flow rate is greater than 1 liter per minute;

wherein said suction flow rate is greater than 1.25 liters per minute;

wherein said suction flow rate is in the range between about 0.5 liters per minute to about 2.0 liters per minute;

wherein said suction flow rate is in the range between about 0.5 liters per minute to about 2.5 liters per minute;

wherein said suction flow rate is in the range between about 0.75 liters per minute to about 2.5 liters per minute.

Figure 10:
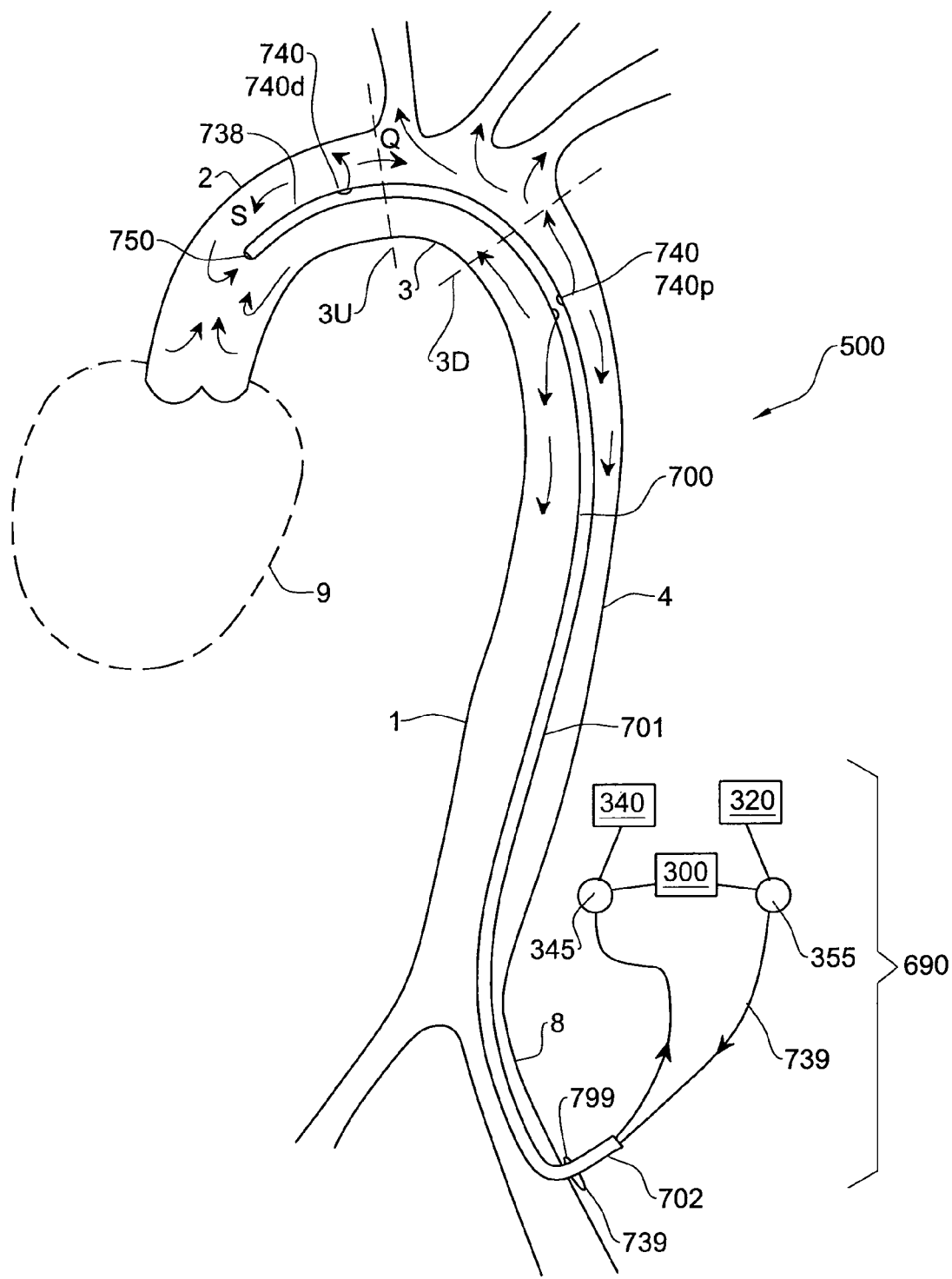
FIG. 10 is a schematic illustration of an aortic system according to a second embodiment of the invention, wherein the respective arterial device is installed in the aorta.
Figure 11:
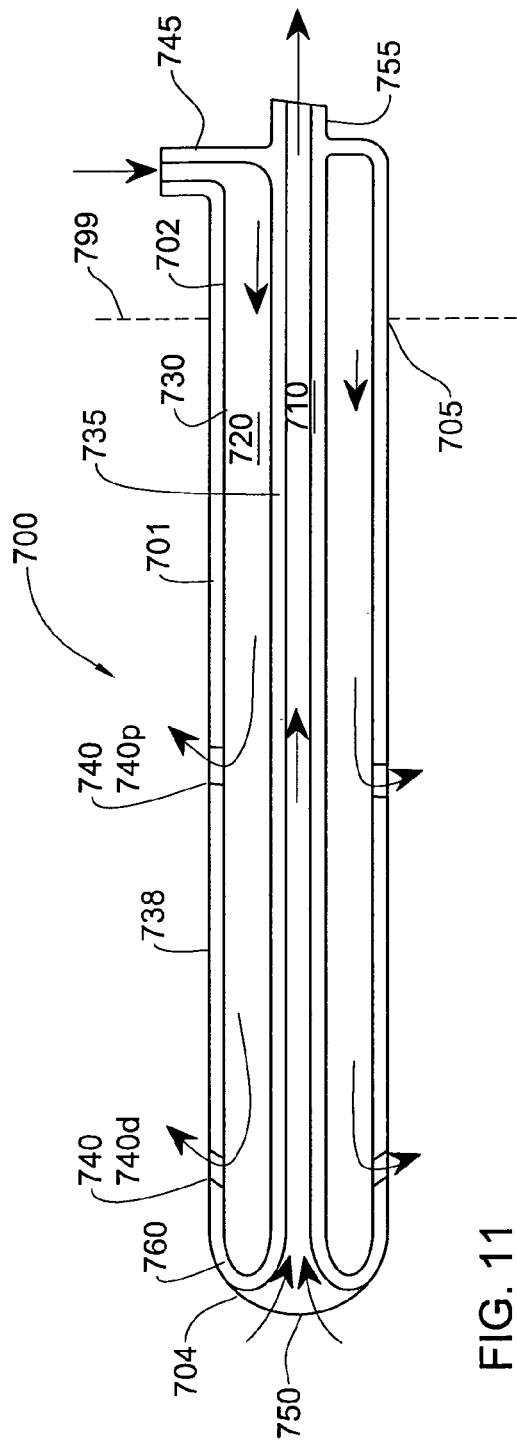
FIG. 11 is a cross-sectional side view of the arterial device of the embodiment of FIG. 10.

Referring to FIGS. 10 and 11, an arterial system according to a second embodiment of the invention, designated herein with the reference numeral 500, comprises all the elements and features of the system according to the first embodiment and/or alternative variations thereof and may be operated in a similar manner thereto and with similar operating parameters, mutatis mutandis, with a number of differences, as follows. In particular, arterial system 700 comprises an arterial device 500 (also referred to interchangeably herein as an aortic device), and controller 300. Controller 300 is as disclosed for the first embodiment, mutatis mutandis, and is operatively connected to, and selectively controls, pump 325 and suction source 345, also as disclosed for the first embodiment, mutatis mutandis.

Arterial device 700 is in the form of an aortic catheter, in particular an intra-aortic double-lumen catheter, configured for being inserted into the aorta 1, in particular the ascending aorta 2, during operation of the system 100, via a suitable insertion point 799, well downstream of the aortic arch 3. In this embodiment, the insertion point 799 is in the femoral artery of the patient, but in alternative variations of this embodiment, the insertion point may instead be one of the iliac arteries 8, or a suitable location in the abdominal portion of the descending aorta 4, or indeed any other suitable point along the descending aorta.

Device 700 comprises two internal lumens—a perfusion lumen 710 and an aspiration or suction lumen 720, and comprises a generally tubular outer wall 730 concentric with a generally tubular inner wall 740. Perfusion lumen 710 is defined in the annular space between the inner wall 735 and the outer wall 730, while suction lumen 720 is defined by the space enclosed by the inner wall 735. At a distal end 704 of the device 700 the suction lumen 720 opens to a suction inlet port 750, while the annular space between the inner wall 735 and the outer wall 730 is closed by end wall 760, indicating the distal end of the perfusion lumen 710. Thus, suction inlet port 750 is distal end of the device 700 and in use the suction inlet port 750 faces in a general upstream direction S of the aorta.

The device 700 comprises a distal portion 701 configured for being accommodated within the aorta, so that in use of the system 500 the distal end 704 is located within the ascending aorta 2 of the patient. A proximal end 705 of the distal portion 701 is located at the entry point 799 in use of the system 500.

The proximal end 705 of the device 700 is contiguous with a proximal portion 702 of the device, and the proximal portion 702 comprises a perfusion inlet port 745 and a suction outlet port 755. The proximal portion 702 thus projects out of the entry point 799 of the body and interfaces with other components of the system 500. The proximal portion 702 is configured for remaining outside of the entry point 799 concurrently when the distal portion 701 is installed in the aorta.

The distal portion 701 further comprises a plurality of perfusion outlet ports, collectively designated 740, laterally or radially disposed on the outer wall 730. One or more perfusion outlet ports 740 are located on the device 700 to be distally of the aortic arch 3, i.e., in the ascending aorta 2, in operation of the device 700, and are also designated herein as distal perfusion outlet ports 740d. Additional one or more outlet ports 740 are located proximally of the distal perfusion outlet ports 740d are designated herein as proximal perfusion outlet ports 740p. In the illustrated embodiment, the proximal perfusion outlet ports 740p are located on the device 700 to be in or just downstream of the aortic arch 3, in the upper portion of the thoracic descending aorta, in operation of the system 500. However, in alternative variations of this embodiment, the proximal perfusion outlet ports 740p may instead be located on the device 700 to be within the aortic arch 3, or in the ascending aorta 2 but downstream of the suction inlet port 750, or in the abdominal portion of the descending aorta 4, in operation of the device. In yet other alternative variations of this embodiment, the proximal perfusion outlet ports 740p are integral with the distal perfusion outlet ports 740d.

Returning to the second embodiment illustrated in FIGS. 10 and 11, the perfusion lumen 710 thus extends contiguously between the perfusion inlet port 745 and the perfusion outlet ports 740, and provides fluid communication therebetween. Similarly, the suction lumen 720 thus extends contiguously from the suction outlet port 755 to the suction inlet port 750, and provides fluid communication therebetween. Furthermore, the perfusion outlet ports 740 are downstream of the suction inlet port 750 (in terms of the antegrade aorta flow).

Device 700 is configured for operating within an artery, in particular the aorta 1, more in particular the ascending aorta 2, in a manner to provide fluid communication between the perfusion outlet ports 740 and the suction inlet port 750 within the artery, aorta or ascending aorta, respectively, via the outside 738 of the distal portion 701 of the device 700.

Thus, distal portion 701 has an outside 738 (also referred to interchangeably herein as an outer surface of the distal portion 701) that in use of the device 700 does not occlude or otherwise obstruct the artery, aorta or ascending aorta in which the distal portion 701 is inserted, in particular within a region of the corresponding blood vessel between the location of the suction inlet port 750 and the location of the perfusion outlet ports 740. Furthermore, the device 700, and in particular the distal portion 701, has an absence of any occlusion arrangement that is otherwise configured for occluding of obstructing the artery, in particular the aorta, more particularly the ascending aorta during use of the device such as to prevent such fluid communication between the perfusion outlet ports 740 and the suction inlet port 750 via the outside 738.

In alternative variations of this embodiment in which the distal portion may be configured with one or more occlusion devices (for example inflatable balloons) positioned at a location inbetween the location of the suction inlet port and the location of the perfusion outlet ports, and having an inoperative state in which the occlusion device does not occlude the blood vessel in which the device is installed, and an operative state in which the occlusion device occludes or blocks the blood vessel, such a device is operated with the occlusion device in the aforementioned inoperative state or at least not in the aforementioned operative state.

At the distal end of the proximal portion 702 there is provided a collar 739. In use of the device 700, collar 739 abuts against an outer surface of the blood vessel in which the device is inserted, via the entry point 799, and may be used to limit the penetration of the device 700 into the aorta so that in this position the distal end 704 is at the desired location within the ascending aorta. Furthermore, the collar 739 may assist in affixing the device 700 to the body.

The device 700 may be formed from substantially rigid and/or semi-rigid and medically compatible materials, including, for example including medically suitable plastics, silicon, rubber or composite materials that are known in the art for use in aortic catheter devices. The device 700 may thus be configured as disposable device, being made from disposable materials and disposed of after use with a patient. Alternatively the device may be configured as an autoclavable or otherwise sterilizable and non-disposable device, and formed from suitable materials.

In a similar manner to that disclosed for the first embodiment, mutatis mutandis, perfusion lumen 710 is configured for providing at least a nominal perfusion flow, i.e., having a nominal perfusion blood flow rate NFR, provided at a nominal flow velocity NFV that is below a threshold value V, and in particular, the perfusion lumen 710 is configured for providing a target perfusion flow having a target perfusion flow rate TFR that is significantly greater than the aforesaid nominal perfusion flow rate NFR by a factor $\Delta$FR, referred to herein the excess perfusion flow rate. Furthermore, the perfusion lumen 710 is configured for providing a maximum target perfusion flow having a corresponding maximum target perfusion flow rate $TFR_{max}$ that is greater than the aforesaid nominal perfusion flow rate NFR by a corresponding maximum excess perfusion flow rate $\Delta FR_{max}$. Thus, in the second embodiment, the perfusion lumen 710 also comprises a minimum cross-sectional flow area that is correspondingly larger than would be otherwise be required for providing only the nominal perfusion flow rate NFR, in order to enable flow rates of up to the aforesaid maximum target perfusion flow rate $TFR_{max}$, but still at the flow velocities which are still below the aforesaid threshold value V.

In a similar manner to that disclosed for the first embodiment, mutatis mutandis, suction lumen 720 has a minimum cross-sectional flow area that is smaller than the minimum cross-sectional flow area of the perfusion lumen 710, and in the second embodiment is configured for providing a suction flow rate SFR that can be varied from zero to a maximum suction flow rate $SFR_{max}$ that is generally similar to the corresponding maximum excess perfusion flow rate $\Delta FR_{max}$.

The perfusion inlet port 745 is configured for being connected to, and thus for receiving oxygenated blood from, a suitable perfusion source 320, as disclosed for the first embodiment, mutatis mutandis. A suitable pump 325, as disclosed for the first embodiment, mutatis mutandis, pumps oxygenated blood from the perfusion source 320 to the device 700, and is configured for providing a controllable perfusion flow rate at least up to the maximum target perfusion flow rate $TFR_{max}$ for the particular patient being treated by system 100, and is variably controllable to provide perfusion flow rates from nominally zero to at least up to the maximum target perfusion flow rate $TFR_{max}$.

Thus, as with the first embodiment, mutatis mutandis, the pump 325 is operatively connected to, and is controlled by, controller 300, and controller 300 is configured for controlling the pump 325 to provide any desired perfusion flow rate in the range between zero and at least the maximum target perfusion flow rate $TFR_{max}$.

The suction outlet port 755 is configured for being connected to, and thus for returning blood to, a suitable suction source 345, as disclosed for the first embodiment, mutatis mutandis, and the suction source 345 is controllable and is operatively connected to, and is controlled by, controller 300.

Thus, as with the first embodiment, mutatis mutandis, the suction source 345 is configured for providing a variably controllable suction flow rate from nominally zero to at least the maximum suction flow rate $SFR_{max}$, and the controller 300 is configured for controlling the suction source 345 to provide any desired suction flow rate in the range between zero and at least the maximum suction flow rate $SFR_{max}$.

In at least some operational modes of the system 500, the suction source 345 sucks or aspirates blood via the device 700 and into a suitable receiving volume 340. As with the first embodiment, mutatis mutandis, in alternative variations of the second embodiment as well, the blood collected at receiving volume 340 may be subsequently suitably processed to remove embolic debris and may be then supplied to the perfusion source 320 to provide a closed system.

Thus, in operation the system 500 comprises arterial device 200 and extra-corporeal circulation system 690, which comprises controller 300, pump 325, perfusion source 320 and suction source 345, and optionally also receiving volume 340.

Extra-corporeal circulation system 690 is thus substantially similar or identical to extra-corporeal system 290 of the first embodiment.

In operation of the system 500, the distal portion 701 is inserted into the aorta 2 via the aforementioned entry point 799 and navigated upstream until the distal end 704 is located within the ascending aorta 2. Surgical procedures for inserting intra-aortic catheters from an entry point in the descending aorta or further downstream such as the iliac arteries or femoral arteries are well known in the art.

System 500 can be operated in a manner similar to that described for the first embodiment, mutatis mutandis, and thus may be operated in the nominal perfusion operating mode (NPOM), in which the system 500 operates to provide oxygenated blood at least at the nominal perfusion flow rate NFR to the body circulation system, and/or in the embolic debris removal operating mode (EROM), in which the system 500 operates to provide oxygenated blood at least at the nominal perfusion flow rate NFR to the body circulation system, while concurrently removing embolic debris and preventing the same from flowing to the aortic arch 3, as disclosed above, mutatis mutandis.

Other than the difference in the method of introducing the aortic device into the aorta, the main difference in operation of the system 500 of the second embodiment, as compared to system 100 of the first embodiment, is that in the second embodiment the perfusion flow provided via the perfusion lumen 710 exists the perfusion lumen at the plurality of perfusion outlet ports 740. In NPOM mode perfusion blood is provided at the nominal perfusion flow rate NFR via the distal perfusion outlet ports 740*d* and the proximal perfusion outlet ports 740*p*, and the flow from the latter may be antegrade and/or retrograde, according to the relative sizes of the distal perfusion outlet ports 740*d* and the proximal perfusion outlet ports 740*p* and their locations in the aorta, so that the arteries that branch off from the aortic arch may receive blood from the distal perfusion outlet ports 740*d* and possibly also from the proximal perfusion outlet ports 740*p*. In EROM mode, the relative sizes of the distal perfusion outlet ports 740*d* and the proximal perfusion outlet ports 740*p* and their locations in the aorta may be such that the proportion P of the target perfusion flow rate TFR that sustains the suction flow rate SFR may be provided solely via the distal perfusion outlet ports 740*d*, while the remainder of the target perfusion to the body circulation system may be provided solely via the proximal perfusion outlet ports 740*p* or may be contributed to also via the distal perfusion outlet ports 74.

Figure 12:
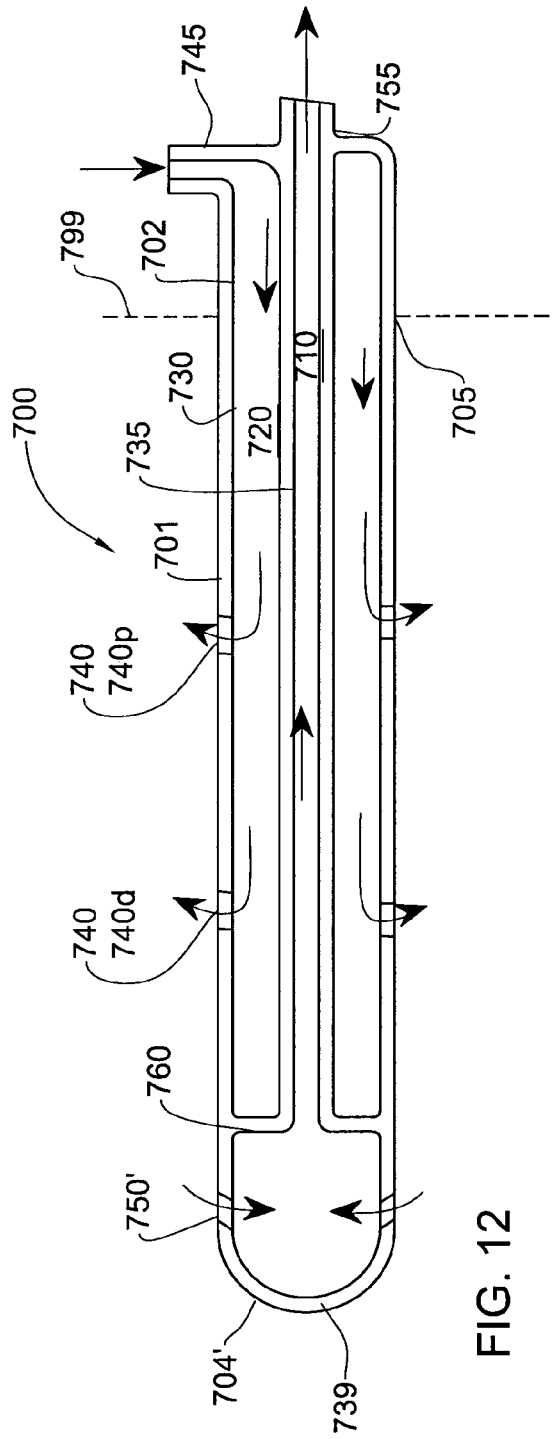
FIG. 12 is a cross-sectional side view of an alternative variation of the arterial device of the embodiment of FIGS. 10 and 11.

In an alternative variation of the second embodiment, illustrated in FIG. 12, the distal end 704' of the device 700 comprises a closed end wall 739 and a tubular wall extension 737 extending distally from outer wall 730 distally of annular wall 760, defining a distal portion of the suction lumen 720. Distal end 704' comprises a plurality of inlet suction ports 750', instead of the single inlet suction port 750 of the second embodiment, and are laterally or radially disposed on the tubular wall extension 737. In this embodiment the suction lumen 720 thus extends contiguously from the suction outlet port 755 to the suction inlet ports 750', and provides fluid communication therebetween.

Installation and operation of the embodiment illustrated in FIG. 12 is similar to that disclosed for the second embodiment illustrated in FIGS. 10 and 11, mutatis mutandis.

Figure 13:
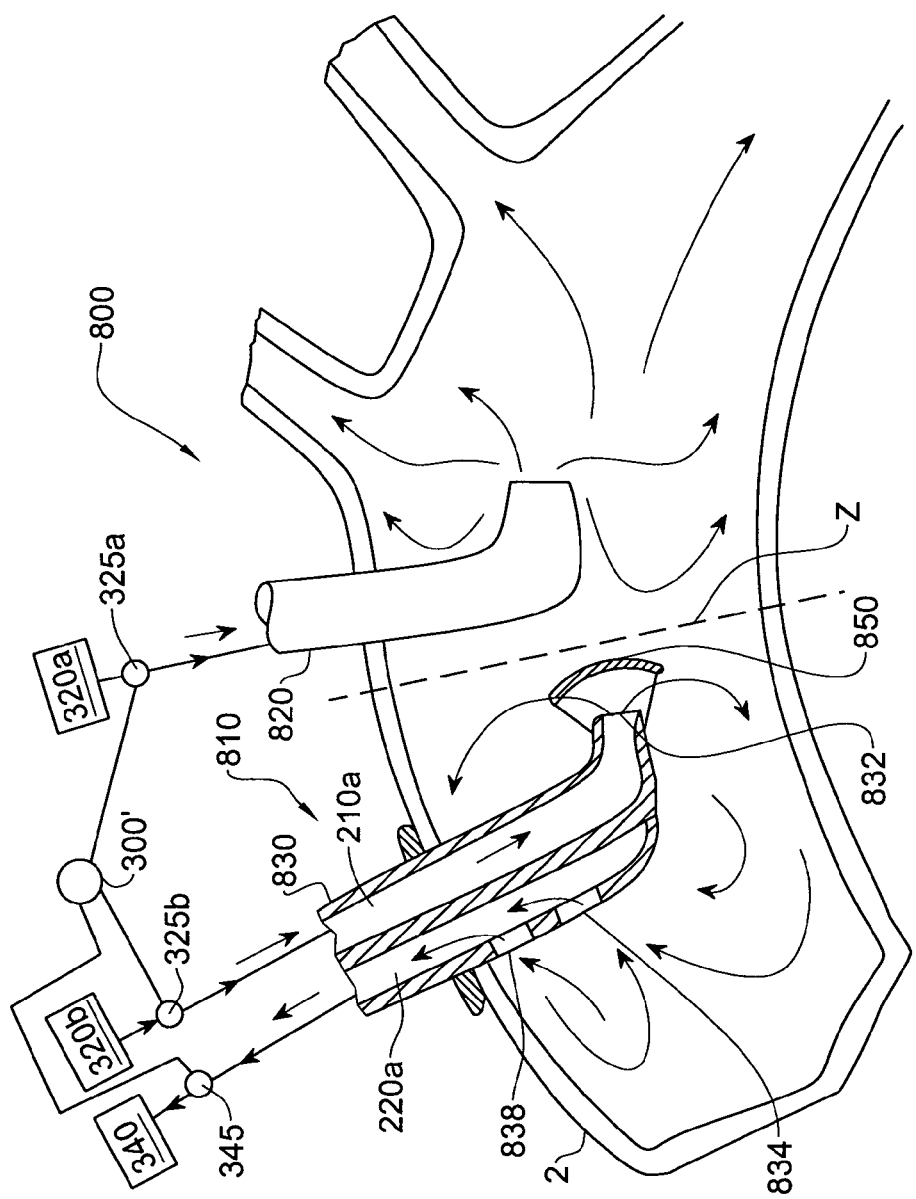
FIG. 13 is a schematic illustration of an aortic system according to a third embodiment of the invention, wherein the respective arterial devices are installed in the aorta.

Referring to FIG. 13, an arterial system according to a third embodiment of the invention, designated herein with the reference numeral 800, comprises all the elements and features of the system according to the first embodiment and/or alternative variations thereof and may be operated in a similar manner thereto and with similar operating parameters, mutatis mutandis, with a number of differences, as follows. In particular, arterial system 800 comprises an arterial fluid exchange system 810, and controller 300'.

In the third embodiment, the function of providing the body with the nominal perfusion flow rate NFR and the function of causing embolic debris to be removed (e.g., by providing a recirculation flow field) are separately performed by two separate arterial devices. Thus, the arterial fluid exchange system 810 comprises an embolic debris removal device 820 and an arterial perfusion cannula 830. Controller 300' is similar to the controller 300 of the first embodiment, mutatis mutandis, but is configured for selectively controlling the fluid flows through embolic debris removal device 820 and arterial perfusion cannula 830.

Arterial perfusion cannula 830 is configured for providing perfusion to the body circulation system, and thus provide the nominal perfusion flow rate NFR. The arterial perfusion cannula 830 is in fluid communication with a suitable perfusion source 320*a* via pump 325*a*, similar to the perfusion source 320 and pump 320 of the first embodiment, mutates mutandis. The perfusion cannula 830 thus has a lumen that is of a suitable size and form to enable the required nominal perfusion flow rate NFR to be supplied to the body circulation system, and controller 300' controls operation of the pump 320*a*, and thus of the nominal perfusion flow rate NFR.

In this embodiment, the arterial perfusion cannula 830 is inserted into the aorta in a manner similar to conventional aortic cannulation devices used for perfusion, and is located downstream of the embolic debris removal device 820.

The embolic debris removal device 820 of this embodiment is similar in form to the aortic device 500 of the first embodiment, and alternative variations thereof, mutatis mutandis, but with some differences as will become clearer herein. The embolic debris removal device 820 thus comprises a distal portion that is inserted into the ascending aorta 2, and comprises a perfusion lumen 210*a* and a suction lumen 220*a*. The perfusion lumen 210*a* is in fluid communication with a second perfusion source 320*b*, via pump 325*b*, similar to the first embodiment, mutatis mutandis. The suction lumen 220*a* is in fluid communication with a suction source such as pump 345 and optionally reservoir 340, as in the first embodiment, mutatis mutandis, and may in all respects be substantially identical to the corresponding components of the first embodiment, mutatis mutandis. The pumps 345 and 325*b* are operatively connected to, and are selectively controlled by, controller 300'.

In alternative variations of this embodiment, a single pump may be used to carry out the functions of pumps 345 and 325*b*.

In alternative variations of this embodiment, first perfusion source 320*a* and second perfusion source 320*b* are integrated into a single perfusion source.

Perfusion lumen 210*a* is similar to the perfusion lumen 210 of the first embodiment, mutatis mutandis, but differs therefrom in that in the third embodiment, the perfusion lumen 210*a* is configured for providing only the excess perfusion flow ΔFR into the aorta, rather than the full target perfusion flow rate TFR. Thus, the internal cross section of the perfusion lumen 210*a* may be correspondingly smaller with respect to the perfusion lumen of the first embodiment, mutatis mutandis.

Thus, while arterial fluid exchange system 810 provides the target flow rate TFR into the aorta, the arterial perfusion cannula 830 is configured for providing the nominal perfusion flow rate NFR while the embolic debris removal device

820 provides the remainder of the target perfusion flow rate, i.e., the excess perfusion flow rate ΔFR.

Arterial system 800 thus operates in a similar manner to the arterial system 100 of the first embodiment, including operating modes such as the EROM and the NPOM mode, as disclosed for the first embodiment, mutatis mutandis, with the main differences including that the excess perfusion flow rate ΔFR is also matched at a desired matching level to the suction flow rate SFR (in a similar manner to that disclosed above for the first embodiment, mutatis mutandis), but via the embolic debris removal device 820, while the nominal perfusion flow NFR is being selectively provided by the arterial perfusion cannula 830 independently thereof. Of course, it is possible to operate the embolic debris removal device 820 to provide an excess perfusion flow rate ΔFR that is higher than the suction flow rate SFR, and thus the excess perfusion flow rate ΔFR will also effectively provide perfusion flow to the body circulation system, or to provide an excess perfusion flow rate ΔFR that is less than the suction flow rate SFR, and concurrently operate the arterial perfusion cannula 830 to provide a perfusion flow rate that is higher than the nominal perfusion flow rate NPR to compensate.

Without being bound by theory, inventors consider that when the excess perfusion flow rate ΔFR is suitably matched to the suction flow rate SFR, and the suction flow rate SFR is above the threshold value discussed above, a substantially self-contained recirculation field may be set up between the perfusion outlet 832 of the perfusion lumen 210*a*, and the suction inlet 834 of the suction lumen 834 of the suction lumen 220*a*, in a similar manner to that discussed above for the first embodiment, mutatis mutandis. However, for this to occur, the arterial perfusion cannula 830 is operated to provide a perfusion flow rate sufficient to effectively or actually create a stagnation zone Z inbetween the locations of the arterial perfusion cannula 830 and the embolic debris removal device 820. The recirculation flow field generated by the embolic debris removal device 820 causes embolic debris that may be present in the aorta to be diverted to the suction inlet 834 and is subsequently removed.

The embolic debris removal device 820 may optionally comprise a flow diverter 250 facing the perfusion outlet 832 and spaced therefrom, to facilitate recirculation of the excess perfusion flow rate ΔFR in a retrograde direction towards the upstream part of the ascending aorta.

A feature of this embodiment or at least one alternative variation thereof is that the perfusion lumen 210*a* of the embolic debris removal device 820 can be designed to be much smaller than the perfusion lumen of the first embodiment, for example, and thus the overall size of embolic debris removal device 820 may be reduced as compared to the aortic device of the first embodiment, for example. Alternatively, the perfusion lumen 210*a* may be of increased size (for example as in the aortic device of the first embodiment) which effectively reduces the flow velocity at the perfusion outlet 832 for a given excess perfusion flow rate ΔFR.

Another feature of this embodiment or at least one alternative variation thereof is that the excess perfusion rate ΔFR can be fully matched (matching level of 100%) to the suction flow rate SFR in the embolic debris removal device 820, which is a separate device to the arterial perfusion cannula 830. Thus, since substantially all the excess perfusion rate ΔFR is effectively recirculated within the ascending aorta and sucked out as the suction flow rate, a perfusion fluid may be used for this that is different from that of the perfusion flow being provided by the arterial perfusion cannula 830. For example, a suitable saline solution or blood plasma may be used as the perfusion fluid provided to the embolic debris removal device 820 instead of oxygenated blood, to provide the excess perfusion rate ΔFR, and this is subsequently removed via the suction lumen 220*a* together with embolic debris. A feature of this arrangement is that it is not necessary to use up valuable oxygenated blood for the purpose of removing the embolic emboli. Another feature of this is that flow velocities may be used for the excess perfusion rate ΔFR can be greater than the threshold velocity referred to above, since the operating fluid is now saline solution (for example) and not blood that could otherwise be damaged.

As in the first embodiment or alternative variations thereof, the embolic debris removal device 820 may comprise an air bubble suction inlet 838 that is particularly configured for removing embolic emboli in the form of air bubbles that may be released into the aorta when the aorta is unclamped, for example, similar an form and function to the air bubble suction inlet of the first embodiment, mutatis mutandis, and thus the embolic debris removal device 820 may be operated as a de-airing device.

Figure 14:
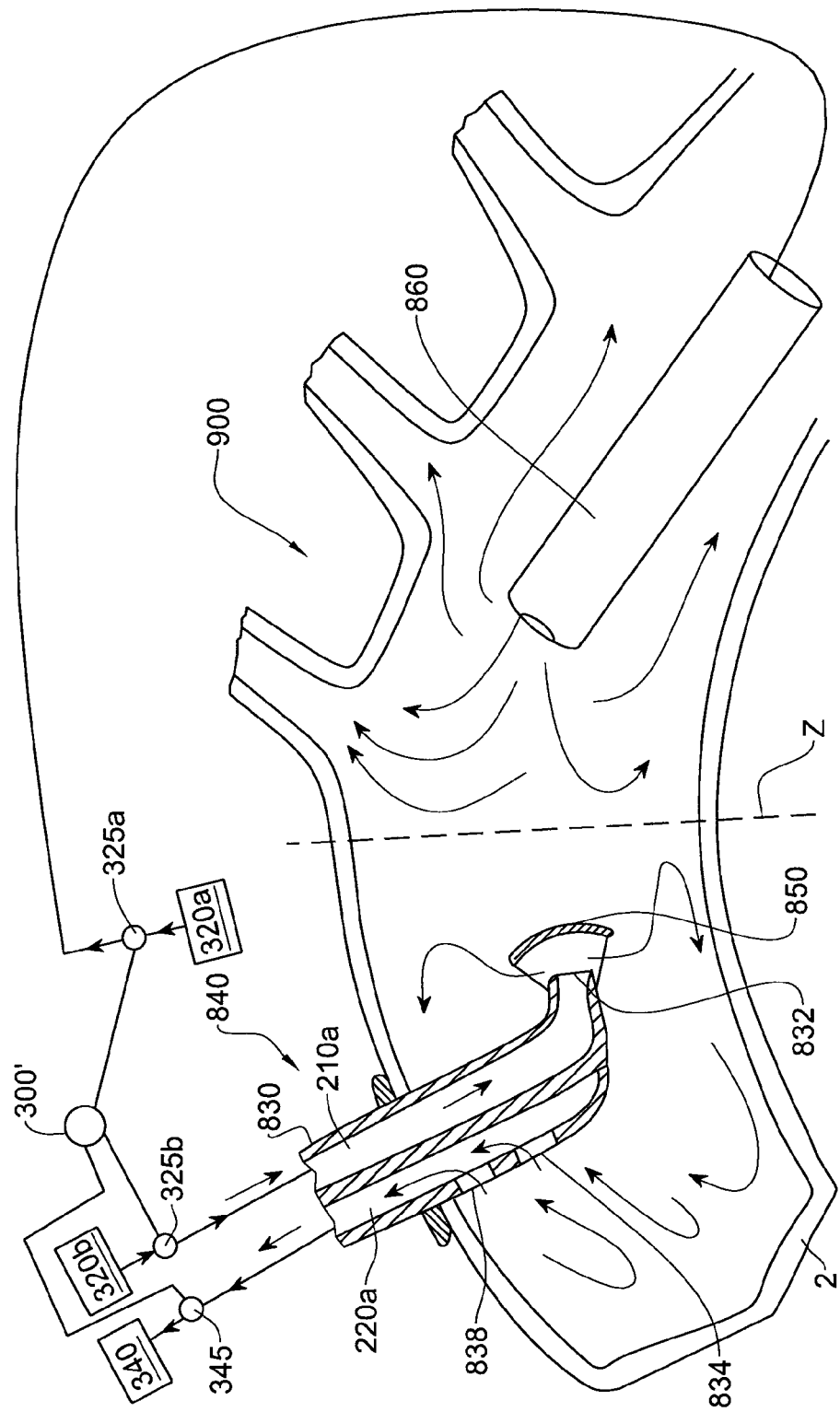
FIG. 14 is a schematic illustration of an aortic system according to a fourth embodiment of the invention, wherein the respective arterial devices are installed in the aorta.

Referring to FIG. 14, an arterial system according to a fourth embodiment of the invention, designated herein with the reference numeral 900, comprises all the elements and features of the system according to the third embodiment and/or alternative variations thereof and may be operated in a similar manner thereto and with similar operating parameters, mutatis mutandis, with a number of differences, as follows. In particular, arterial system 800 comprises an arterial fluid exchange system 840, and controller 300'.

As with the third embodiment, in the fourth embodiment, the function of providing the body with the nominal perfusion flow rate NFR and the function of providing a recirculation flow field to cause embolic debris to be removed are separated and performed by two separate devices. Thus, the arterial fluid exchange system 840 comprises the embolic debris removal device 820, as disclosed for the third embodiment or alternative variations thereof, mutatis mutandis, and an arterial perfusion catheter 860. Controller 300' is as disclosed with respect to the third embodiment, mutatis mutandis.

As with the third embodiment, the perfusion lumen 210*a* is in fluid communication with a second perfusion source 320*b*, via pump 325*b*, and the suction lumen 220*a* is in fluid communication with a suction source such as pump 345 and optionally reservoir 340, and the pumps 345 and 325*b* are operatively connected to, and are selectively controlled by, controller 300'.

Arterial perfusion catheter 860 is configured for providing perfusion to the body circulation system, and thus for providing the nominal perfusion flow rate NFR. The arterial perfusion catheter 860 is similar in function to the arterial perfusion cannula of the third embodiment, and is in fluid communication with perfusion source 320*a* via pump 325*a*, as disclosed for the third embodiment, mutates mutandis. The perfusion catheter 860 thus has a lumen that is of a suitable size and form to enable the required nominal perfusion flow rate NFR to be supplied to the body circulation system, and controller 300' controls operation of the pump 320*a*, and thus of the nominal perfusion flow rate NFR.

In this embodiment, the arterial perfusion catheter 860 is inserted into the aorta in a manner similar to conventional aortic catheter devices used for perfusion, and is located downstream of the embolic debris removal device 820. For example, the arterial perfusion catheter 860 may be inserted into the aorta and navigated into a position in the aortic arch 3, similar to that disclosed herein for the aortic device 700 of the second embodiment, mutatis mutandis.

Arterial system 900 thus operates in a similar manner to the arterial system 800 of the third embodiment, including operating modes such as the EROM and the NPOM mode, and also for de-airing via air bubble suction inlet 838, as disclosed for the third embodiment, mutatis mutandis, with the main differences being that a perfusion catheter is used for providing the nominal flow rate NFR to the body circulation, rather than a perfusion cannula. Accordingly, the arterial system 900 shares many of the features of the arterial system of the third embodiment, and has at least another feature in that it avoids having to provide two entry points at or close to the ascending aorta.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

The invention claimed is:

1. An arterial system, comprising an arterial flow exchange system and a controller, for use with a patient having an aorta and a body blood circulation system, wherein:
said arterial flow exchange system comprises a distal portion arrangement configured for being accommodated in the aorta of the patient in use of the arterial flow exchange system, said distal portion arrangement comprising:
a perfusion lumen arrangement having at least one perfusion outlet and connectable to at least one perfusion source, said perfusion lumen arrangement being configured for providing therethrough a target perfusion flow into the aorta having a target perfusion flow rate that is greater than a nominal perfusion flow rate by an excess perfusion flow rate, wherein said nominal perfusion flow is sufficient for providing adequate fluid flow to the body blood circulation system of the patient; and
a suction lumen arrangement having at least one suction inlet and connectable to a suction source, said suction lumen arrangement being configured for providing a suction flow out of the aorta, said suction flow having a suction flow rate;
said distal portion being configured for providing fluid communication between at least one said perfusion outlet and at least one said suction inlet within the aorta via an outside of said distal portion, in use of the arterial system;
said controller being configured, in use of the arterial system, for:
selectively controllably providing a target perfusion flow into the aorta at said target perfusion flow rate;
selectively controllably providing a suction flow out of the aorta at said suction flow rate; and
selectively controlling said target perfusion flow rate and said suction flow rate concurrently to establish a recirculation flowfield between at least one said perfusion outlet and at least one said suction inlet within the aorta to cause embolic debris that may be present in the aorta to be diverted to said at least one suction inlet.

2. The system according to claim 1, wherein said suction flow rate is a proportion of a said nominal perfusion flow rate, wherein said proportion is not less than about 10% of said nominal perfusion flow rate.

3. The system according to claim 1, wherein said arterial flow exchange system is embodied in an arterial device, and said distal portion arrangement constitutes a distal portion of said arterial device and is configured for being accommodated into the aorta, wherein said arterial device is in the form of an aortic cannula, wherein said distal portion is configured for being introduced into the aorta via a wall of the ascending aorta.

4. The system according to claim 3, wherein said perfusion lumen arrangement comprises a first lumen, wherein said suction lumen arrangement comprises a second lumen, and wherein said first lumen and said second lumen are integrally formed in said distal portion, wherein said first lumen has a first flow cross-section and said second lumen has a second flow cross-section, wherein a cross section ratio between said first flow cross-section and said second flow cross-section is between about 1.10 and about 10.0.

5. The system according to claim 3, wherein said arterial device is in the form of an aortic catheter, wherein said distal portion is configured for being introduced into the aorta via an entry point at a location downstream of the descending aorta, the distal portion being further configured for being navigated upstream to the ascending aorta.

6. The system according to claim 1, wherein said target flow rate is in the range between about 3.3 liters per minute to about 7.5 liters per minute.

7. The system according to claim 1, wherein said suction flow rate is greater than 0.5 liters per minute.

8. An arterial device, for use with a patient having an aorta and a body blood circulation system, the arterial device comprising a distal portion arrangement configured for being accommodated in the aorta of the patient in use of the arterial device, said distal portion arrangement comprising:
a perfusion lumen arrangement having at least one perfusion outlet and connectable to at least one perfusion source, said perfusion lumen arrangement being configured for providing therethrough a target perfusion flow into the aorta having a target perfusion flow rate that is greater than a nominal perfusion flow rate by an excess perfusion flow rate, wherein said nominal perfusion flow is sufficient for providing adequate fluid flow to the body blood circulation system of the patient; and
a suction lumen arrangement having at least one suction inlet and connectable to a suction source, said suction lumen arrangement being configured for providing a suction flow out of the aorta, said suction flow having a suction flow rate;
said distal portion being configured for providing fluid communication between at least one said perfusion outlet and at least one said suction inlet within the aorta via an outside of said distal portion, in use of the arterial device;
wherein the arterial device is configured for enabling said target perfusion flow rate and said suction flow rate to be concurrently and selectively controlled to establish a recirculation flowfield between at least one said perfusion outlet and at least one said suction inlet within the aorta to cause embolic debris that may be present in the aorta to be diverted to said at least one suction inlet.

9. The arterial device according to claim 8, wherein said arterial device is in the form of an aortic cannula, wherein said distal portion is configured for being introduced into the aorta via a wall of the ascending aorta.

10. The arterial device according to claim 9, wherein said distal portion comprises a curved portion and a distal end, wherein said distal end comprises said at least one perfusion outlet, and wherein said curved portion comprises said at least one suction inlet.

11. The arterial device according to claim 9, wherein said perfusion lumen arrangement comprises a first lumen, wherein said suction lumen arrangement comprises a second lumen, and wherein said first lumen and said second lumen are integrally formed in said distal portion, wherein said first lumen has a first flow cross-section and said second lumen has a second flow cross-section, wherein a cross section ratio between said first flow cross-section and said second flow cross-section is not less than about 1.10.

12. The arterial device according to claim 11, wherein said cross section ratio is between about 1.10 and about 10.0.

13. The arterial device according to claim 8, wherein said suction flow rate is greater than 0.5 liters per minute.

14. The arterial device according to claim 8, wherein said suction flow rate is in the range between about 0.5 liters per minute to about 2.0 liters per minute.

15. A method for removing embolic debris from an aorta of a patient having a body blood circulation system, comprising:
  (a) providing an arterial flow exchange system comprising a distal portion arrangement configured for being accommodated in the aorta of the patient in use of the arterial flow exchange system, said distal portion arrangement comprising:
    a perfusion lumen arrangement having at least one perfusion outlet and connectable to at least one perfusion source, said perfusion lumen arrangement being configured for providing therethrough a target perfusion flow into the aorta having a target perfusion flow rate that is greater than a nominal perfusion flow rate by an excess perfusion flow rate, wherein said nominal perfusion flow is sufficient for providing adequate fluid flow to the body blood circulation system of the patient; and
    a suction lumen arrangement having at least one suction inlet and connectable to a suction source, said suction lumen arrangement being configured for providing a suction flow out of the aorta, said suction flow having a suction flow rate; said distal portion being configured for providing fluid communication between at least one said perfusion outlet and at least one said suction inlet within the aorta via an outside of said distal portion, in use of the arterial flow exchange system;
  (b) accommodating said distal portion arrangement in the aorta of the patient so that at least one said suction inlet port is accommodated in the ascending aorta of the patient;
  (c) controllably providing a target perfusion flow into the aorta at said target perfusion flow rate;
  (d) controllably providing a suction flow out of the aorta at said suction flow rate; and
  (e) selectively controlling said target perfusion flow rate and said suction flow rate to establish a recirculation flowfield between at least one said perfusion outlet and at least one said suction inlet within the aorta to cause embolic debris that may be present in the aorta to be diverted to the respective at least one said suction inlet.

16. The method according to claim 15, wherein step (e) comprises:
  selectively matching said suction flow rate with said excess perfusion flow rate according to a desired matching level, defined as a percentage of said suction flow rate with respect to said excess perfusion flow rate, wherein said matching level is about 100%.

17. The method according to claim 15, wherein said suction flow rate is a proportion of a said nominal perfusion flow rate, wherein said proportion is not less than about 10% of said nominal perfusion flow rate.

18. The method according to claim 15, wherein said arterial flow exchange system is embodied in an arterial device, and said distal portion arrangement constitutes a distal portion of said arterial device and configured for being accommodated into the aorta,
  wherein said arterial device is in the form of an aortic cannula, and wherein in step (b) said distal portion is introduced into the aorta via a wall of the ascending aorta.

19. The method according to claim 15, wherein said nominal perfusion flow rate is in the range between about 3 liters per minute to about 5 liters per minute.

20. The method according to claim 15, wherein said target flow rate is in the range between about 3.3 liters per minute to about 7.5 liters per minute.

21. The method according to claim 15, wherein said suction flow rate is greater than 0.5 liters per minute.

22. The method according to claim 15, wherein said suction flow rate is in the range between about 0.5 liters per minute to about 2.0 liters per minute.

23. An arterial device, for use with a patient having an aorta and a body blood circulation system, the arterial device comprising a distal portion arrangement configured for being accommodated in the aorta of the patient in use of the system, said distal portion arrangement comprising:
  a perfusion lumen arrangement having at least one perfusion outlet and connectable to at least one perfusion source, wherein said perfusion lumen arrangement is configured for providing therethrough a perfusion flow having a perfusion flow rate; and
  a suction lumen arrangement having at least one suction inlet and connectable to a suction source, said suction lumen arrangement being configured for providing a suction flow out of the aorta, said suction flow having a suction flow rate;
  wherein said suction flow rate is greater than 0.5 liters per minute; and
  wherein the arterial device is configured for enabling said target perfusion flow rate and said suction flow rate to be selectively controlled to establish a recirculation flowfield between at least one said perfusion outlet and at least one said suction inlet within the aorta to cause embolic debris that may be present in the aorta to be diverted to said at least one suction inlet.

* * * * *